US012622752B2

(12) United States Patent
Owens

(10) Patent No.: US 12,622,752 B2
(45) Date of Patent: May 12, 2026

(54) SELF EXPANDING STENT SYSTEM WITH IMAGING

(71) Applicant: KONINKLIJKE PHILIPS N.V., Eindhoven (NL)

(72) Inventor: Michael Sean Owens, Victoria, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 178 days.

(21) Appl. No.: 17/911,692

(22) PCT Filed: Mar. 8, 2021

(86) PCT No.: PCT/EP2021/055698
§ 371 (c)(1),
(2) Date: Sep. 15, 2022

(87) PCT Pub. No.: WO2021/185604
PCT Pub. Date: Sep. 23, 2021

(65) Prior Publication Data
US 2023/0118551 A1 Apr. 20, 2023

Related U.S. Application Data

(60) Provisional application No. 62/990,503, filed on Mar. 17, 2020.

(51) Int. Cl.
*A61B 34/20* (2016.01)
*A61B 6/12* (2006.01)
(Continued)

(52) U.S. Cl.
CPC ................ *A61B 34/20* (2016.02); *A61B 6/12* (2013.01); *A61B 8/12* (2013.01); *A61B 8/463* (2013.01);
(Continued)

(58) Field of Classification Search
None
See application file for complete search history.

(56) References Cited

U.S. PATENT DOCUMENTS 7,930,014 B2 * 4/2011 Huennekens .......... A61B 8/543
600/467
9,314,226 B2 4/2016 Hancock
(Continued)

FOREIGN PATENT DOCUMENTS

WO 2014100382 A1 6/2014
WO 2014105725 A1 7/2014
(Continued)

OTHER PUBLICATIONS

International Search Report and Written Opinion Dated May 26, 2021 For International Application No. PCT/EP2021/055698 Filed Mar. 8, 2021.
(Continued)

*Primary Examiner* — Jonathan Cwern

(57) ABSTRACT

In exemplary examples, methods and systems for treating vascular disease by implanting a stent within the vasculature and using intravascular imaging to determine and ensure that the stent was property implanted and producing a desirable and effective results is disclosed herein. For example, a system may obtain optical shape sensing data and intravascular imaging data for a blood vessel. The system may process the optical shape sensing data and the intravascular imaging data to generate a three-dimensional model and image of the blood vessel immediately before and immediately after stent implantation into the blood vessel, and perform a precise comparison of the before and after images to ensure that the stent was properly implanted and will produce or is producing a desirable and effective result. The precise comparison may be based on a derived diameter associated with the location at which the stent is placed in
(Continued)

Start /900

Receive signal that stent has been delivered to region of interest /902

Access previously obtained or obtain new intravascular optical shape sensing data at plurality of positions along longitudinal axis of stented region /904

Obtain intravascular ultrasound (IVUS) data at plurality of positions along longitudinal axis of stented region /906

Process optical shape sensing and/or IVUS data /908

Output 3-D image and dimensions of blood vessel at stented region /910

Compare and output of comparison of 3-D images and dimensions of blood vessel at region of interest prior to and post placement of stent /912

End the blood vessel based on the generated pre and post generated three-dimensional models.

17 Claims, 9 Drawing Sheets

(51) Int. Cl.

| | |
|---|---|
| *A61B 8/00* | (2006.01) |
| *A61B 8/12* | (2006.01) |
| *A61B 34/10* | (2016.01) |
| *A61F 2/966* | (2013.01) |

(52) U.S. Cl.
CPC ............ *A61B 8/5261* (2013.01); *A61F 2/966* (2013.01); *A61B 2034/104* (2016.02); *A61B 2034/105* (2016.02); *A61B 2034/2061* (2016.02)

(56) References Cited

U.S. PATENT DOCUMENTS

| | | | |
|---|---|---|---|
| 10,070,827 B2 | 9/2018 | Kemp | |
| 2007/0265637 A1* | 11/2007 | Andreas ................. | A61F 2/966 623/1.11 |

| | | | |
|---|---|---|---|
| 2009/0182405 A1* | 7/2009 | Arnault De La Menardiere ........ | A61F 2/954 623/1.11 |
| 2012/0004537 A1 | 1/2012 | Tolkowsky | |
| 2013/0030295 A1 | 1/2013 | Huennekens | |
| 2014/0180108 A1 | 6/2014 | Rice | |
| 2014/0276028 A1 | 9/2014 | Stigall | |
| 2014/0277365 A1 | 9/2014 | Gillespie | |
| 2016/0007947 A1* | 1/2016 | Spencer ............... | A61B 8/0841 600/424 |
| 2018/0008352 A1* | 1/2018 | Flexman ............... | A61B 34/20 |
| 2018/0014886 A1 | 1/2018 | Flexman | |
| 2018/0325618 A1* | 11/2018 | Justin ..................... | A61B 90/37 |
| 2020/0029932 A1* | 1/2020 | Cohen ..................... | A61B 8/54 |

FOREIGN PATENT DOCUMENTS

| | | |
|---|---|---|
| WO | 2015173704 A1 | 11/2015 |
| WO | 2016/088037 A1 | 6/2016 |
| WO | 2019/121889 A1 | 6/2019 |

OTHER PUBLICATIONS

Shi, et al: "Simultaneous catheter and environment modeling for Trans-catheter Aortic Valve Implantation", IEEE, Sep. 14, 2014.

* cited by examiner

800

Step
706

Determine position of stent delivery device with respect to optical shape sensing wire — 802

Co-register optical shape sensing data and IVUS data — 804

Determine dimensions of blood vessel at region of interest — 806

Generate 3-D model of region of interest including position information of border of lumen of blood vessel at each of a plurality of locations — 808

Step
710

1

SELF EXPANDING STENT SYSTEM WITH IMAGING

CROSS REFERENCE TO RELATED APPLICATIONS

This application is the U.S. National Phase application under 35 U.S.C. § 371 of International Application No. PCT/EP2021/055698 filed Mar. 8, 2021, which claims the benefit of U.S. Provisional Patent Application No. 62/990,503 filed Mar. 17, 2020. These applications are hereby incorporated by reference herein.

FIELD OF THE DISCLOSURE

The systems and devices described herein generally relate to treating and imaging blood vessels. More particularly, the present disclosure is directed to implants and methods and systems for treating vascular disease by implanting a stent within the vasculature and using intravascular imaging to determine and ensure that the stent was property implanted and producing a desirable and effective results.

BACKGROUND

Intravascular ultrasound (IVUS) imaging is widely used in interventional cardiology and peripheral vascular intervention as a diagnostic tool for assessing a diseased vessel, such as an artery or vein, within the human body to determine the need for treatment, to guide the intervention, and/or to assess its effectiveness. An IVUS device, including one or more ultrasound transducers, is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

In contrast, solid-state IVUS catheters carry an ultrasound scanner assembly that includes an array of ultrasound transducers distributed around the circumference of the device connected to a set of transducer control circuits. The transducer control circuits select individual transducers or a combination of transducers for transmitting an ultrasound pulse and for receiving the echo signal. By stepping through a sequence of transmitter-receiver pairs, the solid-state IVUS system may synthesize the effect of a mechanically scanned transducer element but without moving parts. Since there is no rotating mechanical element, the transducer array may be placed in direct contact with the blood and vessel tissue with minimal risk of vessel trauma. Furthermore, because there is no rotating element, the interface is simplified. The solid-state scanner may be wired directly to the imaging system with a simple electrical cable and a standard detachable electrical connector.

IVUS imaging may be utilized before, during, and/or after percutaneous coronary intervention (PCI) or peripheral vascular intervention. For example, IVUS imaging may be used for diagnosis and treatment planning to identify a diseased portion of a blood vessel and determine an appropriate diameter and length for a stent to be positioned within the diseased portion of the blood vessel. In other words, blood vessel and stent diameters and/or lengths may be obtained from intravascular image data (e.g., IVUS imaging and/or optical coherence tomography (OCT)).

IVUS imaging is typically performed with a separate intravascular device prior to stent implantation. After performing the IVUS imaging, the intravascular device is removed from the vasculature, and a stent delivery device is then inserted to implant the stent. If a clinician wishes to view the stent after being implanted, the clinician must first remove the stent delivery device before re-inserting the IVUS intravascular device. And even upon re-insertion, it is difficult for the IVUS intravascular device to perform a precise comparison of the location of interest in the blood vessel before and after stent implantation because the clinician is unable to determine whether the IVUS intravascular device is at the exact location when attempting to perform such comparison. Additionally, stent implantation is typically performed by a clinician viewing two-dimensional views of the vasculature, thereby further increasing the difficulty in performing a before and after comparison. Accordingly, it is desirable to provide one or more systems and/or methods to address these and other shortcomings.

SUMMARY

In at least one exemplary example, a system including one or more processors and memory storing instructions is provided. The instructions, when executed by the one or more processors, cause the processors to create three-dimensional composite images of a diseased or stenosed portion of blood vessel immediately before and immediately after stent implantation to perform a precise comparison of the pre-deployment and post-deployment images to ensure that the stent was properly implanted and will produce or is producing a desirable and effective result, including increasing the volume of blood passing through the stenosed and now-stented region.

In an example, a stent delivery system comprises: a shape sensing wire configured to produce shape sensing data representative of a region of interest in a subject's vasculature; a stent delivery device disposed over the shape sensing wire, wherein the stent delivery device comprises a stent and an imaging element disposed distally of the stent, wherein the imaging element is configured to produce intravascular ultrasound imaging data representative of the region of interest; a computing system comprising: one or more processors; and memory storing instructions that, when executed by the one or more processors, cause the one or more processors to: receive a first plurality of signals corresponding to the shape sensing data; receive a second plurality of signals corresponding to the intravascular ultrasound imaging data; co-register the first signals and the second signals; process the first signals and the second signals to generate a pre-deployment three-dimensional model of the region of interest; based on the pre-deployment three-dimensional model, determine a pre-deployment size characteristic of the region of interest; receiving a stent-deployment signal indicative of the stent being deployed; receive a third plurality of signals corresponding to the shape sensing data after receiving the stent-deployment signal; receive a fourth plurality of signals corresponding to the intravascular ultrasound imaging data after receiving the stent-deployment signal; co-register the third signals and the fourth signals; process the third signals and the forth signals to generate a post-deployment three-dimensional model of the region of interest; based on the post-deployment three-dimensional model, determine a post-deployment size characteristic of the region of interest; calculate a comparison of the pre-deployment size characteristic and the post-deployment size characteristic; and provide, to a monitor, the comparison.

In another example, the stent delivery system of the previous paragraphs, wherein the stent delivery device comprises a sensor, wherein the sensor produces the stent deployment signal upon retraction of a sheath over the stent delivery device.

In another example, the stent delivery system of any of the previous paragraphs, wherein the initial size characteristic the updated size characteristic are based on a derived diameter.

In another example, the stent delivery system of any of the previous paragraphs, wherein the derived diameter is based on an area, a volume, or a perimeter of the region of interest.

In another example, the stent delivery system of any of the previous paragraphs, wherein the derived diameter is based on the area of the region of interest.

In another example, the stent delivery system of any of the previous paragraphs, wherein the derived diameter is based on the volume of the region of interest.

In another example, the stent delivery system of any of the previous paragraphs, wherein the derived diameter is based on the perimeter of the region of interest.

In another example, the stent delivery system of any of the previous paragraphs, wherein the derived diameter is based on at least two of an area, a volume, and a perimeter of the region of interest.

In another example, the stent delivery system of any of the previous paragraphs, further comprising a fluoroscopy imaging device to produce fluoroscopic image data corresponding to the region of interest.

In another example, the stent delivery system of any of the previous paragraphs, wherein the memory storing instructions that, when executed by the one or more processors, further cause the one or more processors to co-register fluoroscopic image data with the first signals and the second signals and process the fluoroscopic image data with the first signals and the second signals to generate the pre-deployment three-dimensional model of the region of interest.

In another example a system comprises: one or more processors; and memory storing instructions that, when executed by the one or more processors, cause the one or more processors to: obtain a first plurality of signals corresponding to shape sensing data for a region of interest in a subject's vasculature; obtain a second plurality of signals corresponding to intravascular ultrasound imaging data for the region of interest; co-register the first signals and the second signals; process the first signals and the second signals to generate a pre-deployment three-dimensional composite image of the region of interest; based on the pre-deployment three-dimensional composite image, determine an initial volume of blood capable of passing through the region of interest; receiving a stent-deployment signal indicative of a stent being deployed in the region of interest; receive a third plurality of signals corresponding to the shape sensing data after receiving the stent-deployment signal; receive a fourth plurality of signals corresponding to the intravascular ultrasound imaging data after receiving the stent-deployment signal; co-register the third signals and the fourth signals; process the third signals and the forth signals to generate a post-deployment three-dimensional composite image of the region of interest; based on the post-deployment three-dimensional model, determine an updated volume of blood capable of passing through the region of interest; calculate a comparison of the initial volume of blood and the updated volume of blood; and provide a comparison signal indicative of the comparison.

In another example, a non-transitory computer readable medium storing instructions for execution by one or more processors incorporated into a system, wherein execution of the instructions by the one or more processors cause the one or more processors to: obtain initial optical shape sensing data for a blood vessel; obtain initial intravascular imaging data for the blood vessel; co-registering the initial optical shape sensing data and the initial intravascular imaging data; generate an initial three-dimensional model from the initial optical shape sensing data and the initial intravascular imaging data; determine an initial derived diameter associated with a portion of the initial three-dimensional model; obtain subsequent intravascular imaging data for the blood vessel; co-registering the initial optical shape sensing data and the subsequent intravascular imaging data; generate an subsequent three-dimensional model from the initial optical shape sensing data and the subsequent intravascular imaging data; determine an subsequent derived diameter associated with a portion of the subsequent three-dimensional model; and provide, to a monitor, a signal representative of a comparison of the initial derived diameter and the subsequent derived diameter.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, examples, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, examples, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, examples, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular examples illustrated herein.

DETAILED DESCRIPTION

Before any examples of the disclosure are explained in detail, it is to be understood that the disclosure is not limited in its application to the details of construction and the arrangement of components set forth in the following description or illustrated in the following drawings. The disclosure is capable of other examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
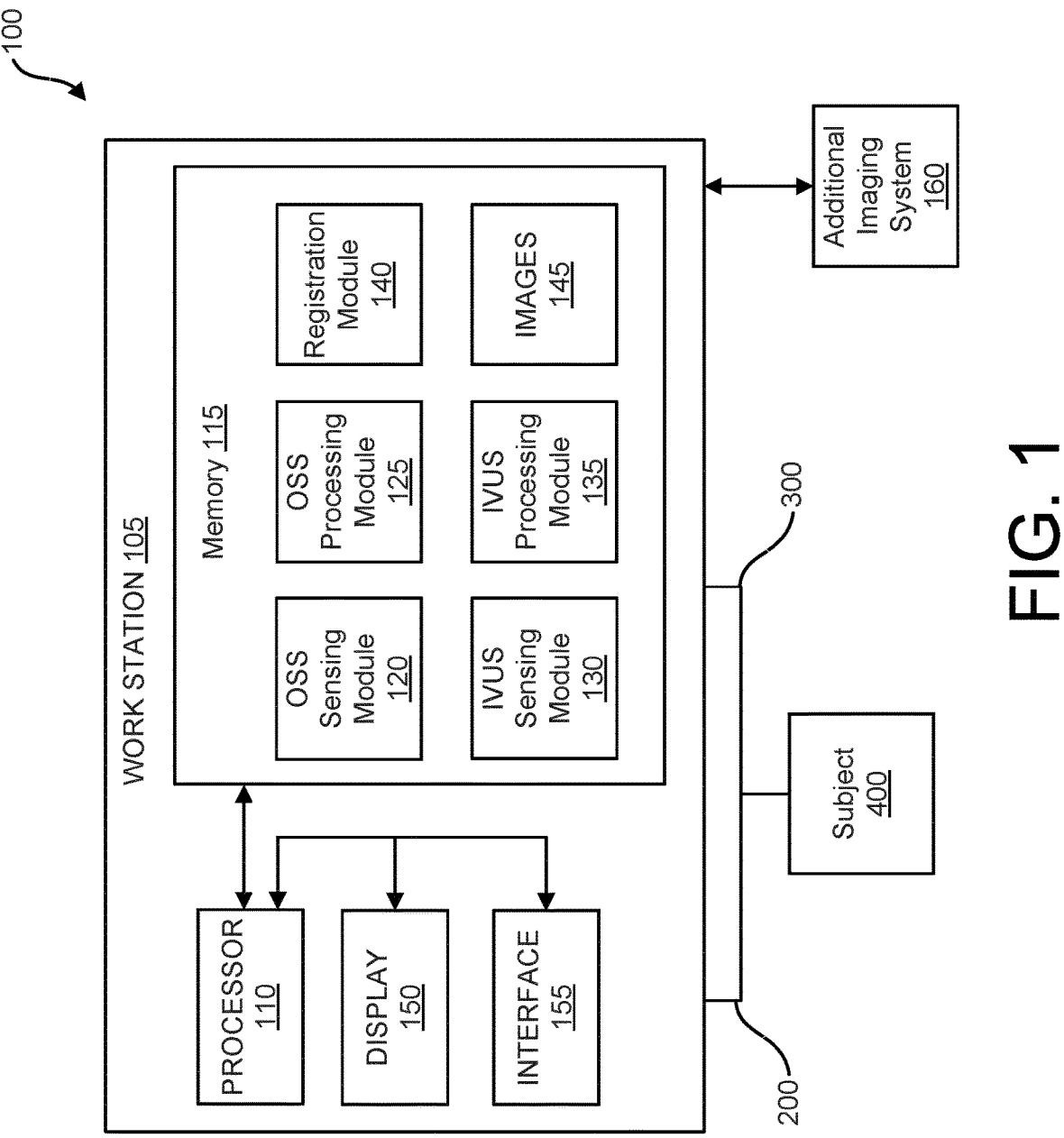
FIG. 1 is an exemplary block diagram illustrating a stent delivery system that includes imaging according to an example of the present disclosure.

Referring to FIG. 1, there is depicted an exemplary block diagram illustrating a system 100 that is capable of delivering and deploying a stent. The system 100 for deploying a stent, such as a self-expanding stent, uses navigation and imaging enabled technology to precisely measure the vessel and/or a region of interest in the vessel and create a three-dimensional image or model thereof prior to stent implantation (e.g., a pre-deployment three-dimensional image or model), deploy the stent, and precisely measure the vessel and/or a region of interest in the vessel and/or stent and create a three-dimensional image or model thereof after stent implantation (e.g., a post-deployment three-dimensional image or model). The navigation may be manually or robotically performed. System 100 may include a workstation or console 105 from which a clinician performs, supervises and/or manages the stent delivery procedure. The workstation 105 preferably includes a computer system comprising one or more processors 110 and memory 115 for storing programs and applications to perform the methods disclosed herein.

Memory 115 may store an optical sensing module 120 and an OSS processing module 125. The optical sensing module 120 may be configured to interpret optical feedback signals from one or more optical shape sensing ("OSS") devices or wires 300 and produce intravascular optical shape sensing data. Optical sensing module 120 may also be configured to use the optical signal feedback (and any other feedback, e.g., electromagnetic (EM) tracking) to reconstruct deformations, deflections and other changes associated with a medical device or instrument, which is passed through a deployment device or system, such as a stent deployment device 200. The OSS processing module 125 may be configured to generate, based on the intravascular optical shape sensing data, a three-dimensional (3D) OSS image at each of the plurality of positions across the region of interest and outputting the OSS images to the monitor (e.g., a display device and/other another type of user interface device) 150 to portray a 3D image of the vessel and/or a region of interest of the vessel.

The stent deployment device 200 may include a tube or main body 210 through which the OSS wire 300, which acts as a guidewire is passed. The OSS wire 300 includes one or more optical fibers, which in turn are connected to the workstation 105. The OSS wire 300 and optical fibers are employed to provide a visual representation of the deployable component, such as an stent. While described in terms of the stent, the present principles can also apply to other implantables.

Figures 2, 3:
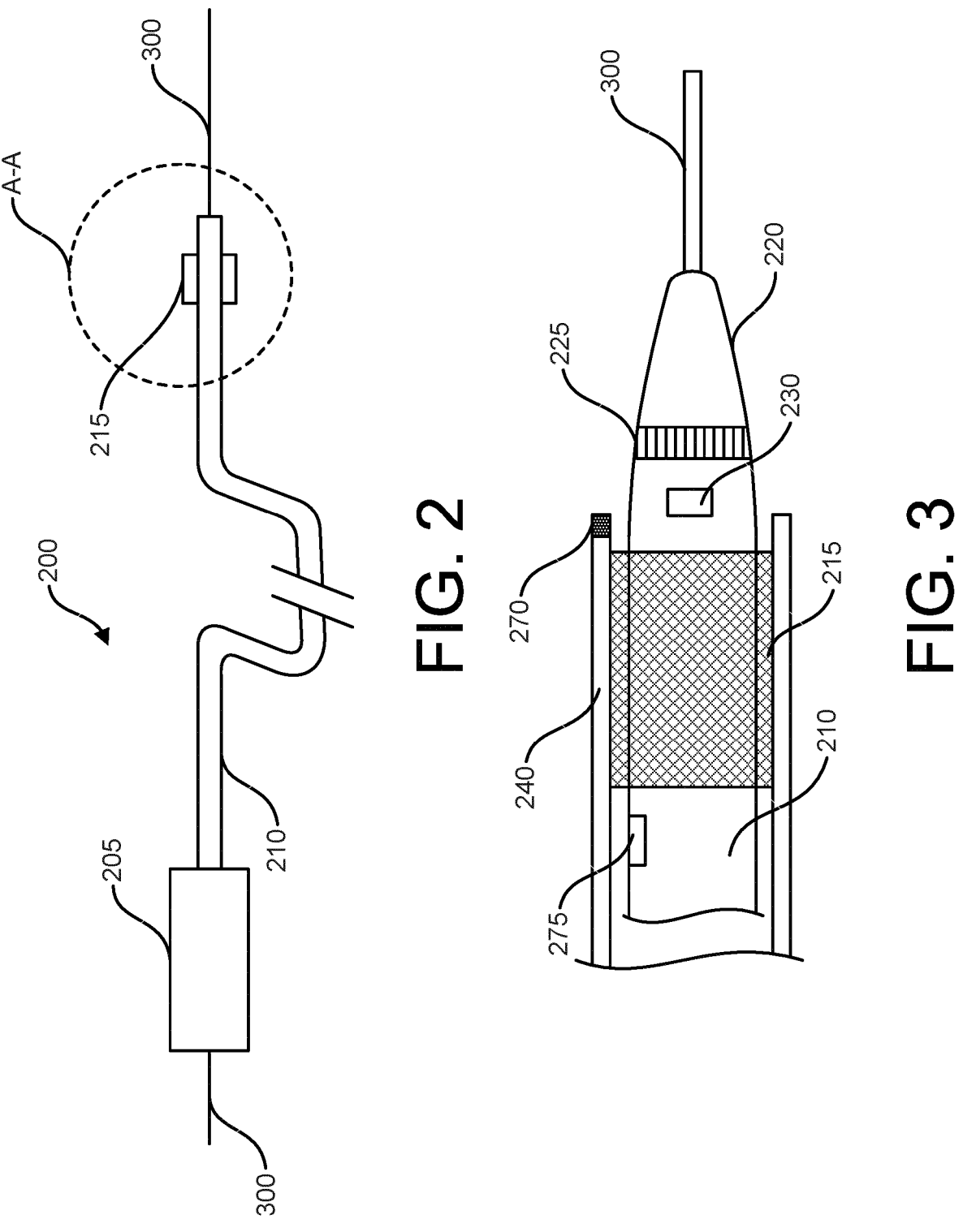
FIG. 2 is an exemplary longitudinal schematic view of a stent delivery device and optical shape sensing wire of the stent delivery system according to an example of the present disclosure.
FIG. 3 is an enlarged longitudinal side view of the distal portions of the stent delivery device and optical shape sensing wire taken along line A-A in FIG. 2 with the stent attached to the shaft of the stent delivery device.

In one example, the optical fibers of the OSS wire 300 are integrated within or through the OSS wire 300. The OSS wire 300 can be employed for making physical measurements. The measurements may be employed for planning or for placement of the stent. As illustrated in FIGS. 2 and 3, the stent delivery device 200 is placed over the OSS wire 300. As such, the handle 205 of the stent delivery device 200 is coupled to the OSS wire 300. As will be discussed in more detail below, the location and/or position of the stent delivery device 200, including the location and/or relative position of the stent 215, relative to the OSS wire 300 is registered in the registration module 140. That is, relative locations and/or positions of the OSS wire 300, the stent delivery device 200, and the stent 215 are co-registered in the registration module 140. As such, any movement of the stent delivery device 200 and the stent 215 is tracked with respect to the OSS 300.

While the present principles may be applied to any interventional guidewire used in combination with a stent, the present disclosure employs the OSS wire 300 to act as the guidewire. Hence, OSS wire 300 acts as a 'delivery rail' for the stent delivery device 200, and the OSS wire 300 passes down a dedicated guidewire lumen within the stent delivery device 200. Since the OSS wire 300 is physically inside the stent delivery device 200, the reconstructed shape of the OSS wire is representative of the shape of the stent delivery device 200. However, the OSS wire 300 is free to rotate and translate inside the stent delivery device 200, and therefore, the precise position and orientation of stent delivery device 200 and/or the stent 215 may be known.

The OSS wire 300 may include fiber optic Bragg grating sensors in one or more optical fibers. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, strain causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

It should be understood that optical shape sensing may be performed in a plurality of ways and is not limited to FBGs or Rayleigh scatter techniques. For example, other techniques may include channels etched into the fiber, employing quantum dots for reflection, employing a plurality of separate fibers (e.g., 3 or more) instead of a single multicore fiber or other optical shape sensing techniques.

The OSS wire 300 is registered with the registration module 140 in the memory 115 of the workstation 105. Referring again to FIG. 1, a registration module 140 is configured to register the OSS wire 300 to the stent delivery device 200, an additional imaging system 160, a physical structure (e.g., stenosis, etc.) within the vasculature, other images, etc. For shape recognition registration, a distinctive shape or shape template can be employed to obtain both position and orientation information from the fiber. If the fiber takes a predefined and immutable path, the curvature and shape information of that path can be used to identify a unique image to fiber transformation to be stored in memory 115 (i.e., images 145) because the OSS processing module 125 may be configured to generate, based on the intravascular optical shape sensing data, a plurality of 3D OSS images at each of the plurality of positions across the region of interest that can be used for subsequent verification and comparisons.

An image processing module 135 is configured to combine 3D OSS images 145 and OSS wire 300 position data for joint or separate display on the display 150. The OSS position data and the image data (from pre-operative or intraoperative images 145) can be registered and jointly displayed to assist in placement of the stent (or other implantable device). An imaging system 160 may include a fluoroscopy system (x-rays) for collecting real-time visual information about positions of instruments or anatomical features. Images 145 collected with the imaging device 160 may be registered with the OSS data from OSS wire 300.

By using an OSS wire and/or a portion of the stent deployment device 200, e.g., the handle 205, and thus the position of the stent 215 (or at least the relevant markers on the endograft), the navigation can be simplified. Then, navigation can be performed using the registered pre-operative (e.g., CT) images for guidance. To introduce the use of optical shape sensing into an interventional procedure, it is first necessary to integrate the fiber into one or more of the devices/systems used for the intervention. By integrating optical shape sensing into the OSS wire 300 used during stent deployment and registering the stent 215 and stent deployment device 200 to the OSS wire 300 in accordance with the present principles, the system 100 can be used with any type of stent and/or deployment system with limited impact on design of the stent or the deployment mechanism.

Workstation 105 may include a display 150 for viewing internal images of a subject (patient) 400 may include images 145 (preoperative or intraoperative images) or OSS data as an overlay or other rendering registered with the OSS wire 300 in one or more of the components employed in the procedure. Display 150 may also permit a user to interact with the workstation 105 and its components and functions (e.g., touchscreen, graphical user interface, etc.), or any other element within the system 100. This is further facilitated by an interface 155 which may include a keyboard, mouse, a joystick, a haptic device, or any other peripheral or control to permit user feedback from and interaction with the workstation 105.

One step in stent deployment is the positioning of x-ray visible (radiopaque) markers. These are initially positioned when the stent 215 is advanced via the stent delivery device 200 over the OSS wire 300 to the approximate location of interest in the blood vessel 405. If the stent 215 can be semi-deployed, then the markers are re-used to fine tune the position of the stent 215. Placement of a three-dimensional stent 215 within a three-dimensional anatomy is challenging and is typically performed under two-dimensional imaging guidance through x-ray fluoroscopy. As a consequence, the procedural time for placement of the stent 215 can become very long. The devices, system(s) and methods of the present disclosure potentially reduce the procedural time and immediately confirm the effectiveness of stent implantation.

Figures 4, 5:
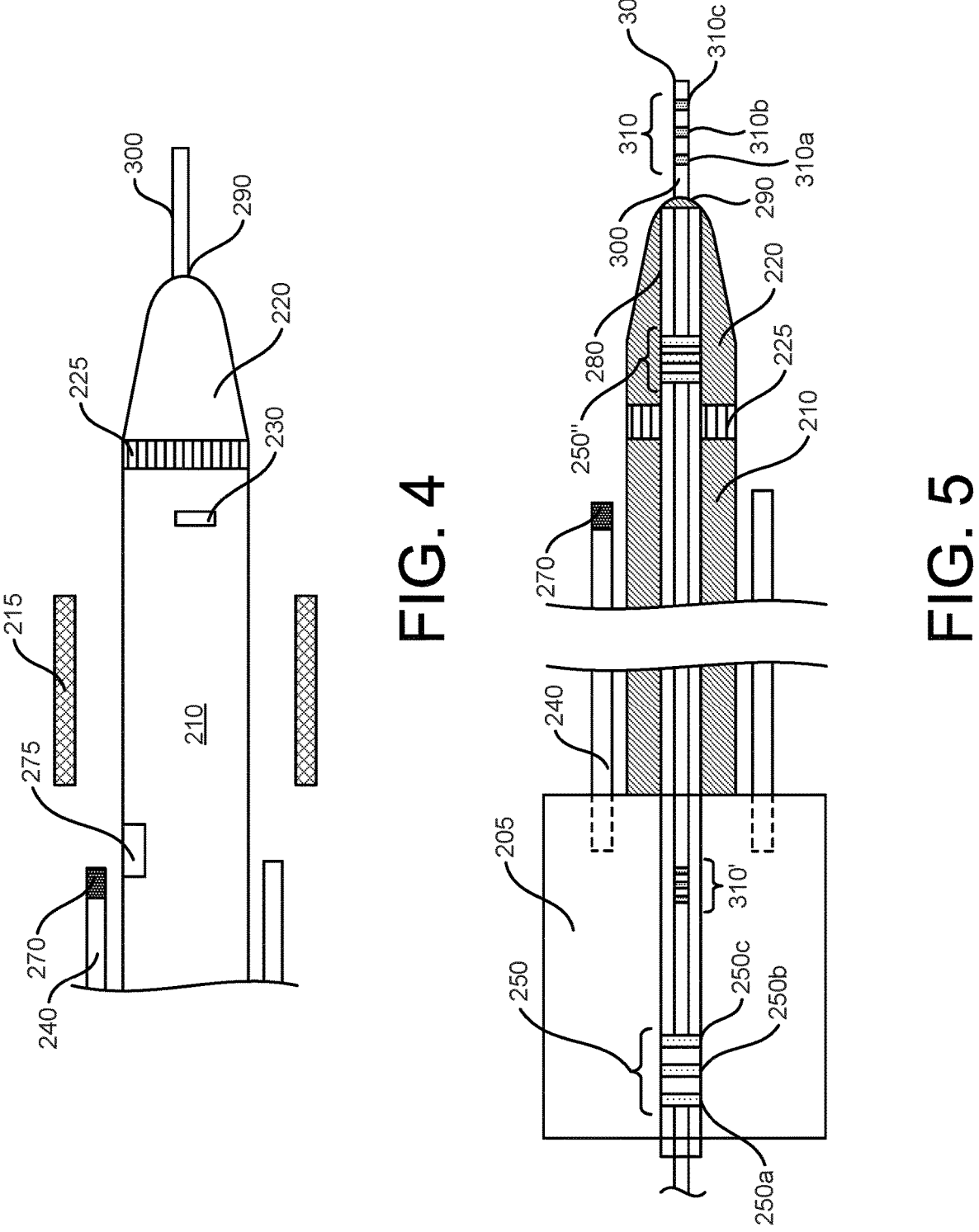
FIG. 4 is an enlarged longitudinal side view of the distal portions of the stent delivery device and optical shape sensing wire taken along line A-A in FIG. 2 with the stent detached from the shaft of the stent delivery device.
FIG. 5 is an exemplary cross-sectional view of the proximal and distal portions of a stent delivery device and optical shape sensing wire of the stent delivery system according to an example of the present disclosure.

Referring to FIG. 2, the deployment device 200 may include one or more control or stabilizing handles 205 that are employed, depending on the design to perform a plurality of tasks, e.g., retract an outer sheath 240 that covers the stent 215 during introduction into the subject's vasculature, advance a shaft 210 carrying the stent 215, adjust the OSS wire 300 or any other useful function depending on the design of the stent deployment device 200 and the functions its needs to carry out. Referring to FIG. 3, there is depicted an enlarged longitudinal side view of the distal portions of the stent delivery device 200 and OSS wire 300 taken about line A-A in FIG. 2 with the stent 215 attached to the shaft 210 of the stent delivery device 200, due at least in part, because the outer sheath 240 retains the self-deploying stent 215 in a collapsed configuration. Referring to FIG. 4, the outer sheath 240 has been retracted proximally relative to the self-deploying stent 215 and the shaft 210 (or the shaft 210 and the self-deploying stent 215 have been extended distally of the outer sheath 240), such that the self-deploying stent 215 is able to expand radially to an expanded configuration. Continuing to refer to FIG. 3, the outer sheath 240 includes a sensor 270 at its distal end, and the shaft 210 of the stent delivery device 200 includes a sensor 275. Upon the outer sheath 240 being retracted proximally relative to the self-deploying stent 215 and/or the shaft 210 (or the shaft 210 and the self-deploying stent 215 being extended distally of the outer sheath 240) the sensor 270, 275 overlap, and one or both sensors send a signal to the workstation 105, wherein the sensor signal(s) are indicative that the stent 215 has been deployed within the vasculature of the subject 400.

The configuration of the stent deployment device 200 is such that one handle 205 may be connected to the stent 215 in an axially and torsionally stiff manner. This permits re-orientation of the stent 215 intra-operatively but can also be re-purposed to maintain a registration between the OSS wire 300 and the stent deployment device 200. This can be achieved in several different ways.

In accordance with examples of the present disclosure, a method and system are described to determine, identify, and/or derive a vessel diameter measurement (e.g., a true/derived diameter measurement) that is used for vessel and stent sizing operations and/or procedures using intravascular imaging (e.g., by using IVUS and/or OCT imaging systems). Exemplarily IVUS systems are disclosed in U.S. Pat. No. 7,930,014 (filed Jan. 11, 2006, titled VASCULAR IMAGE CO-REGISTRATION), U.S. application Ser. No. 14/594, 599 (filed Jan. 12, 2015, titled DETECTING ENDOLEAKS ASSOCIATED WITH ANEURYSM REPAIR), and U.S. application Ser. No. 14/798,218 (filed Jul. 13, 2015, titled DEVICES, SYSTEMS, AND METHODS FOR IMPROVED ACCURACY MODEL OF VESSEL ANATOMY), the entire disclosures of which are expressly incorporated by reference herein.

Figure 6A:
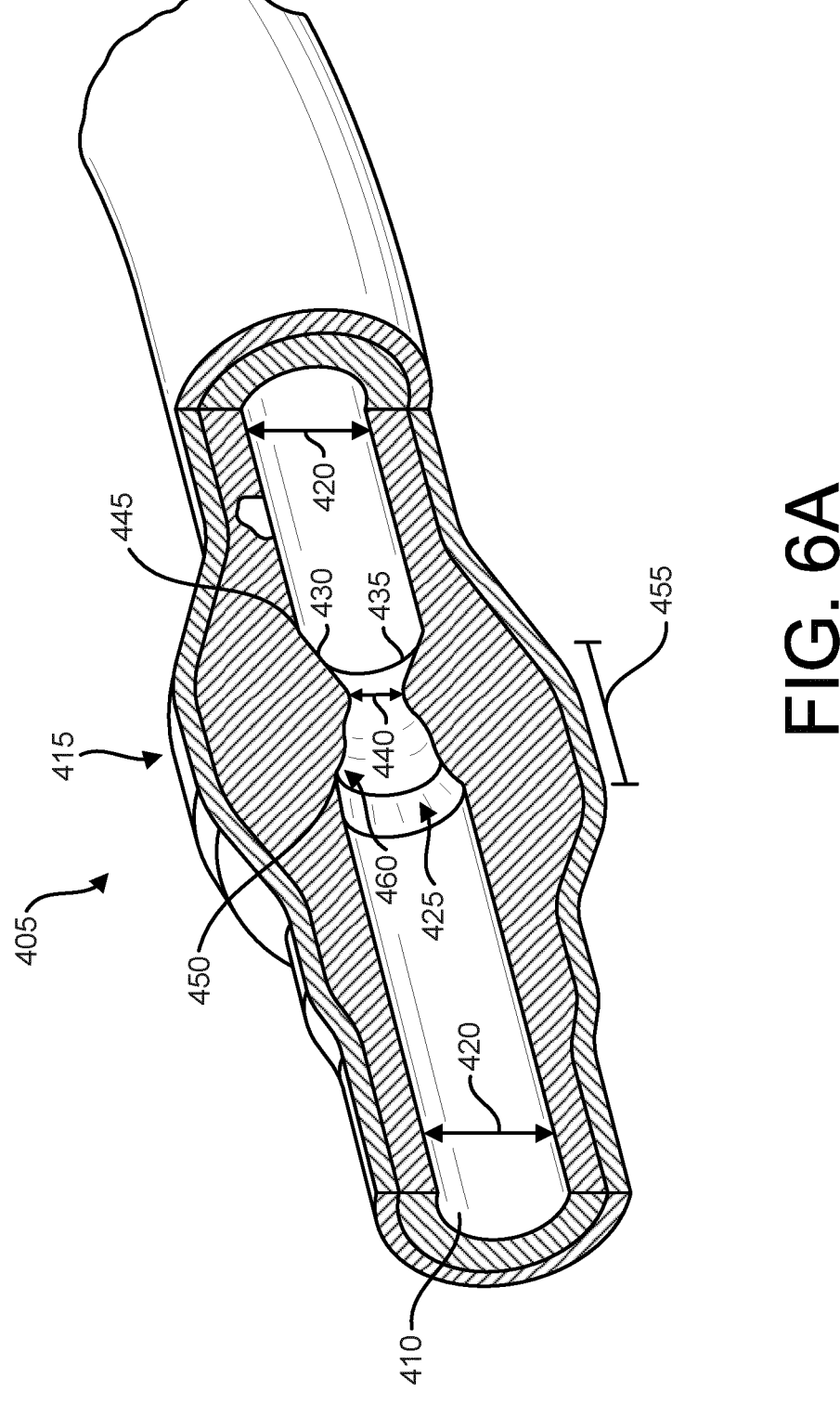
FIG. 6A is an exemplary, partial cross-sectional perspective view of a blood vessel having a stenosis according to an example of the present disclosure.

FIG. 6A shows a vessel 405 having a stenosis. For example, FIG. 6A is a partial cross-sectional perspective view of the vessel 405. The vessel 405 includes a proximal portion on the left side of the figure and a distal portion on the right side of the figure. A lumen 410 extends along the length of the vessel 405 between the proximal portion and the distal portion. In that regard, the lumen 410 allows flow of fluid through the vessel. In some instances, the vessel 405 is a blood vessel. In some instances, the vessel 405 is a coronary artery, a peripheral artery or a peripheral vein. In such instances, the lumen 410 is configured to facilitate the flow of blood through the vessel 405.

As shown, the vessel 405 includes a stenosis 415 between the proximal portion and the distal portion. Stenosis 415 is generally representative of any blockage or other structural arrangement that results in a restriction to the flow of fluid through the lumen 410 of the vessel 405. Examples of the present disclosure are suitable for use in a wide variety of vascular applications, including coronary, peripheral (including but not limited to lower limb, carotid, and neurovascular), renal, and/or venous. Where the vessel 405 is a blood vessel, the stenosis 415 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Continuing to refer to FIG. 6A, the lumen 410 of the vessel 405 has a diameter 420 proximal of the stenosis 415 and a diameter 470 distal of the stenosis. In some instances, the diameters 420 and 470 are substantially equal to one another. In that regard, the diameters 420 and 470 may represent healthy portions, or at least healthier portions, of the lumen 410 in comparison to stenosis 415. Accordingly, these healthier portions of the lumen 410 are illustrated as having a substantially constant cylindrical profile and, as a result, the height or width of the lumen has been referred to as a diameter. However, it is understood that in many instances these portions of the lumen 410 will also have plaque buildup, a non-symmetric profile, and/or other irregularities, but to a lesser extent than stenosis 415 and, therefore, will not have a cylindrical profile. In such instances, the diameters 420 and 470 are understood to be representative of a relative size or cross-sectional area of the lumen and do not imply a circular cross-sectional profile. In some examples, diameters 420 and 470 might not have equal diameters, but may still represent healthy portions (e.g., in examples when the vessel 405 is a vein). In other words, in such examples, healthy portions may also be represented by other criteria for example—area, plaque burden, eccentricity (e.g., mathematical eccentricity of a conic section that uniquely characterizes its shape eccentricity based on a measure of deviation from circularity), etc.

As shown in FIG. 6A, stenosis 415 includes plaque buildup 425 that narrows the lumen 410 of the vessel 405. In some instances, the plaque buildup 425 does not have a uniform or symmetrical profile, making angiographic evaluation of such a stenosis unreliable. In the illustrated example, the plaque buildup 425 includes an upper portion 430 and an opposing lower portion 435. In that regard, the lower portion 435 has an increased thickness relative to the upper portion 430 that results in a non-symmetrical and non-uniform profile relative to the portions of the lumen proximal and distal of the stenosis 415. As shown, the plaque buildup 425 decreases the available space for fluid to flow through the lumen 410. In particular, the cross-sectional area of the lumen 410 is decreased by the plaque buildup 425. At the narrowest point between the upper and lower portions 430, 435 the lumen 410 has a height 440, which is representative of a reduced size or cross-sectional area relative to the diameters 420 and 470 proximal and distal of the stenosis 415. The stenosis 415 may longitudinally extend between a proximal shoulder 450 and a distal shoulder 445. The shoulders 450, 445 may be areas where the plaque buildup 425 begins/ends. A length of the stenosis 415 may be defined by the length between the proximal shoulder 450 and the distal shoulder 445. Note that the stenosis 415, including plaque buildup 425 is exemplary in nature and should not be considered limiting in any way. In that regard, it is understood that the stenosis 415 has other shapes and/or compositions that limit the flow of fluid through the lumen 410 in other instances. While the vessel 405 is illustrated in FIG. 6A as having a single stenosis 415 and the description of the examples below is primarily made in the context of a single stenosis, it is nevertheless understood that the devices, systems, and methods described herein have similar application for a vessel having multiple stenosis regions.

In some examples, instead of plaque buildup 425, the lumen 410 of the vessel 405 may also be narrowed based on other factors. For example, in peripheral vasculature (e.g., veins), the narrowing of the lumen 410 may be caused by compression from an external vessel (e.g., pressure from an external artery). As such, method(s) described below may also be used to determine a derived diameter of the vessel 405 that has been compressed due to the external vessel and/or other factors.

Treatment of the stenosis 415 may include the positioning of a stent 215 within the lumen 410. The stent 215 may be configured to reestablish a normal or near-normal flow of fluid through the lumen 410 by increasing the size or cross-sectional area of the lumen 410. That is, referring to FIG. 6B, the stent 215 may increase the height 440' at the narrowest point between the upper and lower portions 430, 435 to be greater than that shown in FIG. 6A. In some examples, the diameter of the stent 215 may be approximately equal to the diameters 420 or 470. The stent 215 may extend between the proximal shoulder 450 and the distal shoulder 445. A length of the stent 215 may be similar to the length of the stenosis. The proximal and distal ends of the stent 215 may include stent struts that are well opposed to a lumen wall 450 when the stent 215 is properly positioned within the lumen 410. The stent struts may be positioned near the proximal shoulder 445 and the distal shoulder 450.

In order to determine a proper treatment plan for deploying the stent within the vessel 405, including for determining the length and/or diameter of a stenosis and/or determining a proper length and/or diameter of the stent, a separate imaging system 160 may be used. The separate imaging system 160 may include an intravascular device such as a catheter, guide wire, or guide catheter. At a high level, the intravascular device may be a separate intravascular ultrasound device (IVUS), such as a rotational IVUS device or a solid-state IVUS device. In that regard, the IVUS device may emit ultrasonic energy from the imaging element(s) or transducer element(s) included in scanner assembly mounted near a distal end of the IVUS device. The rotational IVUS device may include one imaging element or transducer element. The solid-state IVUS device may include an array of imaging elements or transducer elements.

Alternatively, referring to FIGS. 3 and 4, the intravascular device for determining the length and/or diameter of a stenosis may be the stent delivery device 200 with IVUS capability included therein. For example, the stent delivery device 200 may include an array of transducer elements 225 may be positioned in an annular configuration about a longitudinal axis of the. The emitted ultrasonic energy is reflected by tissue structures in the medium surrounding the scanner assembly, and the ultrasound echo signals are received by the transducer element(s) 225. In some examples, the transducer element(s) may be positioned adjacent a distal portion 220 of the stent delivery device 200. In that regard, the transducer element(s) 225 may be positioned less than 30 cm, less than 10 cm, less than 5 cm, less than 3 cm, less than 2 cm, and/or less than 1 cm from a distal tip of the stent delivery device 200. It is understood that the transducer element(s) 225 may be positioned at any position along the stent delivery device 200, including any distance from the distal tip. In some instances, the transducer element(s) 225 may be positioned at the distal tip of the stent delivery device 200. It is preferable, however, that the transducer element(s) 225 be positioned at the distal tip of the stent delivery device 200 at a position distal to the axial position of the stent 215 when the stent 215 is coupled to the shaft 210 in a collapsed configuration, as shown in FIG. 3. It is understood that the stent delivery device 200 may be positioned distal to the stenosis 415 in the vessel 405 and prior to the deployment of the stent 215, and prior to (and after) such deployment, the stent delivery device 200 is pulled back manually or in an automated manner to image the plaque buildup 425.

The scanner assembly 225 may include integrated circuit controller chip(s) configured to activate transmitter circuitry to generate an electrical pulse to excite the transducer element(s) and to accept amplified echo signals received from the transducer element(s) via amplifiers included on the integrated circuit controller chip(s). In examples in which the stent delivery device 200 includes the transducer array 225, the integrated circuit controller chips(s) may be configured to select the particular transducer array element(s) to be used for transmitting and/or receiving. The processing architecture of the integrated circuit controller chips(s) may be similar to the one described in U.S. Provisional Application No. 61/746,804, filed Dec. 28, 2012, the entirety of which is hereby incorporated by reference. The frequency of the transmit signal from the transducer element(s) may be controlled by the integrated circuit controller chips an IVUS processing module 135 in the memory 115 of the workstation 105 and/or another module in the workstation 105.

The integrated circuit controller chips(s) may be configured to excite the transducer element(s) to emit ultrasonic energy with multiple frequencies at each A-scan. The transducer element(s) may be configured to emit the various frequencies to optimize the information gathered about components within the vessel 405, such as blood, plaque, adventitia, calcium, stent struts, etc. The various frequencies may interrogate respective components of the vessel 405 with improved accuracy. For example, a low-frequency A-array may be used to detect high-density objects (e.g., stents, calcium) at low-gain reception and plaque/adventitia at high-gain reception. Low-frequency A-scans may be in the range of about 5 MHz to about 30 Mhz, about 5 Mhz to about 25 Mhz, about 10 Mhz to about 30 Mhz, and/or other suitable values. For example, a high-frequency A-array may detect fine detail in the tissue areas. High-frequency A-scans may be in the range of about 30 Mhz to about 80 Mhz, about 30 Mhz to about 70 Mhz, about 40 Mhz to about 80 Mhz, and/or other suitable values. Low-gain reception may be 10 dB to 40 dB lower than the high-gain reception, depending on the system's dynamic range. While two frequency ranges-a high-frequency range and a low-frequency range— and two gain ranges-high-gain reception and low-gain reception—are described herein, it is understood that any number of frequency ranges and/or gain ranges may be utilized. The multi-frequency IVUS imaging data may be combined to identify more clearly the different components of the vessel 405 as described in, for example, U.S. Provisional Patent Application No. 61/740,822, filed Dec. 21, 2012, the entirety of which is hereby incorporated by reference herein.

The stent delivery device 200 may be configured to detect blood flow within the vessel 405. For example, the integrated circuit controller chip(s) and/or IVUS processing module 135 may be configured to control the transducer element(s) 225 to emit ultrasonic energy with the same frequency for the same A-array in a non-consecutive manner. For example, successive emissions with the same frequency (e.g., different samples of the same A-scan) may be separated in time. In that time, blood would have moved across the transducer element(s), while stationary tissue would not have. Thus, by separating ultrasonic firings for the transducer element(s) in time, blood may be identified where the IVUS imaging data indicates movement and tissue may be identified where there is no movement. The samples may be separated by a period in the range of about 60 μsec to about 150 μs, 70 μsec to about 135 μs, 80 μs to about 120 μs, and/or other suitable values. The sample period may be selected based on, e.g., the blood flow rate. The change in the IVUS imaging data over the period between firings may be analyzed to determine if the change is suggestive of blood flow within a wedge of the field of view associated with the A-scan. If the difference in the samples is more than the expected noise or interference, then the IVUS imaging data may be representative of blood flow. Blood flow information may be extracted as described in, for example, U.S. patent application Ser. No. 13/974,757, filed Aug. 23, 2013, the entirety of which is hereby incorporated by reference herein.

The IVUS imaging data collected using multiple frequencies and firings separated in time may be combined to generate a more accurate model of vessel anatomy. For example, blood may be identified as areas that have little or no signal reception at low frequency A-scans. Stents and calcium may be identified as those areas that have reasonable signal strength at low-gain reception of low-frequency A-Scans. Tissue regions may be imaged using high-frequency A-scans, but a model of the vessel anatomy may include information from all exposures (e.g., low frequency with high gain, low frequency with low gain, high frequency, etc.) to generate a more accurate data representation or visual representation of the tissue and reduce blood and/or tissue speckle.

The workstation 105 may include the IVUS processing module 135 that facilitates communication of signals between the IVUS sensing module 130 and the scanner assembly included in the transducer 225. This communication may include, among others, the steps of: (1) providing commands to the integrated circuit controller chip(s), (2) providing the transmit trigger signals to the integrated circuit controller chip(s) to activate the transmitter circuitry to generate an electrical pulse to excite transducer element(s), and (3) accepting amplified echo signals received from the transducer element(s) via amplifiers included on the integrated circuit controller chip(s). In some examples, the IVUS processing module 135 performs preliminary processing of the echo data prior to relaying the data to the IVUS sensing module 130. For example, the IVUS processing module 135 performs amplification, filtering, and/or aggregating of the data. In some examples, the PIM 304 also supplies high- and low-voltage DC power to support operation of the transducer 225. The IVUS processing module 135 transmits (e.g., provides and/or transfers) the received echo signals to the IVUS sensing module 130 where, among other things, the ultrasound image may be reconstructed and displayed on the monitor or display 150.

The IVUS processing module 135 may receive the echo data from the transducer 225 by way of the IVUS sensing module 130 and process the data to reconstruct an image of the tissue structures in the medium surrounding the transducer 225. The echo data may be used to generate a mixed-mode IVUS image including both B-array and flow information. The B-array image represents the two-dimensional anatomical structure of the tissue in a plane perpendicular to the longitudinal axis of transducer 225, with brightness at any point of the image representing of the strength of the echo signal received from the corresponding location within the tissue. Flow data is associated with a visual representation of movement of elements in the medium surrounding the scanner such as blood flow. B-mode data (e.g., using the multi-frequency ultrasonic emissions) and flow data (e.g., using ultrasonic emission separated in time) may be collected, processed, and/or combined as described herein. The computing system 306 may also output the mixed mode image on the monitor or display 150.

The workstation 105 may be generally representative of any device suitable for performing the processing and analysis techniques discussed within the present disclosure. In some examples, the workstation 105 includes at least one processor, random access memory, and/or storage medium. In that regard, in some instances the memory 115 is programmed to execute steps associated with the data acquisition and analysis described herein. Accordingly, it is understood that any steps related to data acquisition, data processing, instrument control, and/or other processing or control aspects of the present disclosure may be implemented by the computing systems using corresponding instructions stored on or in a non-transitory computer readable medium accessible by the computing device. In some instances, the workstation 105 is a console device. In some instances, the workstation 105 is similar to the S5™ Imaging System or the S5i™ Imaging System, each available from Volcano Corporation. In some instances, the workstation 105 is portable (e.g., handheld, on a rolling cart, etc.). Further, it is understood that in some instances the workstation 105 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

The additional imaging system 160 may include the angiographic/fluoroscopic imaging system that is configured to generate a two-dimensional representation of the vessel 405. The angiographic/fluoroscopic imaging system may include an x-ray source. For example, a reference image of the vessel 405 may be generated by the angiographic/fluoroscopic imaging system with a radiopaque contrast agent injected into the vessel 405.

Angiographic/fluoroscopic image data may be received at the workstation 105. For example, the workstation may include a video capture card. The angiographic/fluoroscopic image data may be output to the monitor or display 150. The angiographic/fluoroscopic image data may be combined with the IVUS imaging data to generate a high accuracy model of the vessel 405. In some examples, the IVUS imaging data and the angiographic/fluoroscopic image data may be simultaneously collected (e.g., during automated or manual pullback of the stent delivery device 200). For example, the IVUS imaging data and the angiographic/fluoroscopic image data may be co-registered as described in, for example, U.S. patent application Ser. No. 13/632,916, filed Oct. 1, 2012 published as U.S. Patent Application Publication No. 2013/0030295 on Jan. 31, 2013; and/or U.S. patent application Ser. No. 13/228,229, filed Sep. 8, 2011 published as U.S. Patent Application Publication No. 2012/0004537 on Jan. 5, 2012, the entireties of which are incorporated by reference. That is, an IVUS image may be correlated to a location of the stent 215 delivered by the stent delivery device 200 within the vessel 405 using the angiographic/fluoroscopic image data. The registration module 140 may be configured to carry out the processing steps associated with co-registering with the IVUS imaging data and the angiographic/fluoroscopic image data.

Referring to FIGS. 3 and 4, in some examples, the distal portion of the shaft 210 of the stent delivery device 200 may include one or more orientation markers 230. In some examples, the shaft 210 of the stent delivery device 200 may include a plurality of orientation markers 230. The orientation markers 230 may be made of a radiopaque material such that orientation markers 230 are visible in the angiographic/fluoroscopic image data. The orientation markers 230 may be used to determine a longitudinal position of the shaft 210 of the stent delivery device 200 along the vessel 405 in the angiographic/fluoroscopic image data. The orientation markers 230 used to determine an orientation, rotational position, and/or angular rotation of the intravascular device about its own longitudinal axis. Thus, the cross-section of the vessel 405 being imaged may be determined using the orientation markers 230 as described herein. In some examples, the shaft 210 of the stent delivery device 200 may include three orientation markers 230 that are equally spaced apart around the circumference of the shaft 210 of the stent delivery device 200. For example, the three orientation markers 230 may be spaced about 120° apart around the circumference of the shaft 210 of the stent delivery device 200. In such examples, at least one of the three orientation markers 230 is visible in any angiographic/fluoroscopic image data. In some examples, the orientation markers 230 themselves may be made of the radiopaque material. In some examples, a band around the circumference of the stent delivery device 200 may be made of a radiopaque material. The orientation markers may be notches or cutouts of the radiopaque band. The orientation markers 230 may be positioned proximal to (as shown in FIGS. 3 and 4) or distal to the transducer element(s) 22.

The orientation markers 230 may be non-symmetrically shaped, such as a sawtooth shape. The sawtooth shape may include one side that extends parallel to a longitudinal axis of the stent delivery device 200 and one side that extends obliquely with respect to the longitudinal axis. As the stent delivery device 200 is rotated in the direction towards the top, the angled side will appear towards the top in angiographic/fluoroscopic image data. Similarly, as the stent delivery device 200 is rotated in the direction towards the bottom, the angled side will appear towards the bottom. The IVUS processing module 135 may thus determine whether the transducer 225 device is rotated towards the front of the vessel 405 or the back. The IVUS processing module 135 may measure the distance from the top or bottom of the stent delivery device 200 to the parallel side of the orientation maker 230 to determine the angle at which stent delivery device 200 is rotated. Whether the stent delivery device 200 is rotated towards the front or back and the rotational angle may be used to determine a cross-section of the vessel 405 or the wedge of the total field of view of the stent delivery device 200 being imaged. The sawtooth shape is a non-limiting example, and different shapes may be used in different examples.

A co-registered IVUS image may be rotated based on the rotational angle of the stent delivery device 200 determined using the orientation marker 230. In some instances, a width or diameter 420, 470 of the lumen 410 may be measured in the angiographic/fluoroscopic image data. The width or diameter 420, 470 of the lumen 410 in the co-registered IVUS image is expected to the same. The measured width may provide a starting point for determining a position and contours of the lumen wall in the co-registered IVUS image. For example, the IVUS processing module 135 may be configured to use this information to carry out a border detection algorithm. The border detection algorithm is likely to provide a more accurate result when a seed point, such as the measured width or diameter from the angiographic/fluoroscopic image data, is used, as opposed to when the border detection algorithm must first guess a starting point and then follow the border. Thus, the knowledge of the cross-section of the vessel 405 being imaged by the transducer, coupled with knowledge of the position of the stent delivery device 200 within the vessel 405, may be used to make a high accuracy determination of the diameter and cross-sectional area of the vessel 405.

In some examples, the stent delivery device 200 includes some features similar to traditional rotational IVUS catheters, such as the Revolution® catheter available from Volcano Corporation. In some examples, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the stent delivery device 200 includes the scanner assembly 225 near its distal end, and a transmission line bundle extending along the longitudinal body of the stent delivery device 200. The transmission line bundle terminates in a patient interface module (PIM) connector at a proximal end of the stent delivery device 200. The PIM connector electrically couples the transmission line bundle to the PIM and physically couples the stent delivery device 200 to the PIM. In an embodiment, the stent delivery device 200 further includes a guide wire exit port 290. Accordingly, in some instances the stent delivery device 200 is a rapid-exchange catheter. The guide wire exit port 290 allows a OSS wire 305 to be inserted towards the distal end in order to direct the stent delivery device 200 through the vessel 405.

In some examples, the stent delivery device 200 is configured to image within the vessel 405 while being moved through the lumen 410. In some instances, the stent delivery device 200 is configured to be moved through the lumen 410 and across the stenosis 415. Thus, IVUS imaging data may be collected at a plurality of positions across the region of interest of the vessel 405. The region of interest may include the stenosis 415. In that regard, the stent delivery device 200 is positioned distal of the stenosis 415 and moved proximally (i.e., pulled back) across the stenosis to a position proximal of the stenosis in some instances. In other instances, the stent delivery device 200 is positioned proximal of the stenosis 415 and moved distally across the stenosis to a position distal of the stenosis. Movement of the stent delivery device 200, either proximally or distally, is controlled manually by medical personnel (e.g., hand of a surgeon) in some examples. In other examples, movement of the stent delivery device 200, either proximally or distally, is controlled automatically by a movement control device (e.g., a pullback device, such as the Trak Back® II Device available from Volcano Corporation). In that regard, the movement control device controls the movement of the stent delivery device 200 at a selectable and known speed (e.g., 2.0 mm/s, 1.0 mm/s, 0.5 mm/s, 0.2 mm/s, etc.) in some instances. Movement of the IVUS device 302 through the vessel is continuous for each pullback or push through, in some instances. In other instances, the stent delivery device 200 is moved step-wise through the vessel (i.e., repeatedly moved a fixed amount of distance and/or a fixed amount of time).

Figure 7:
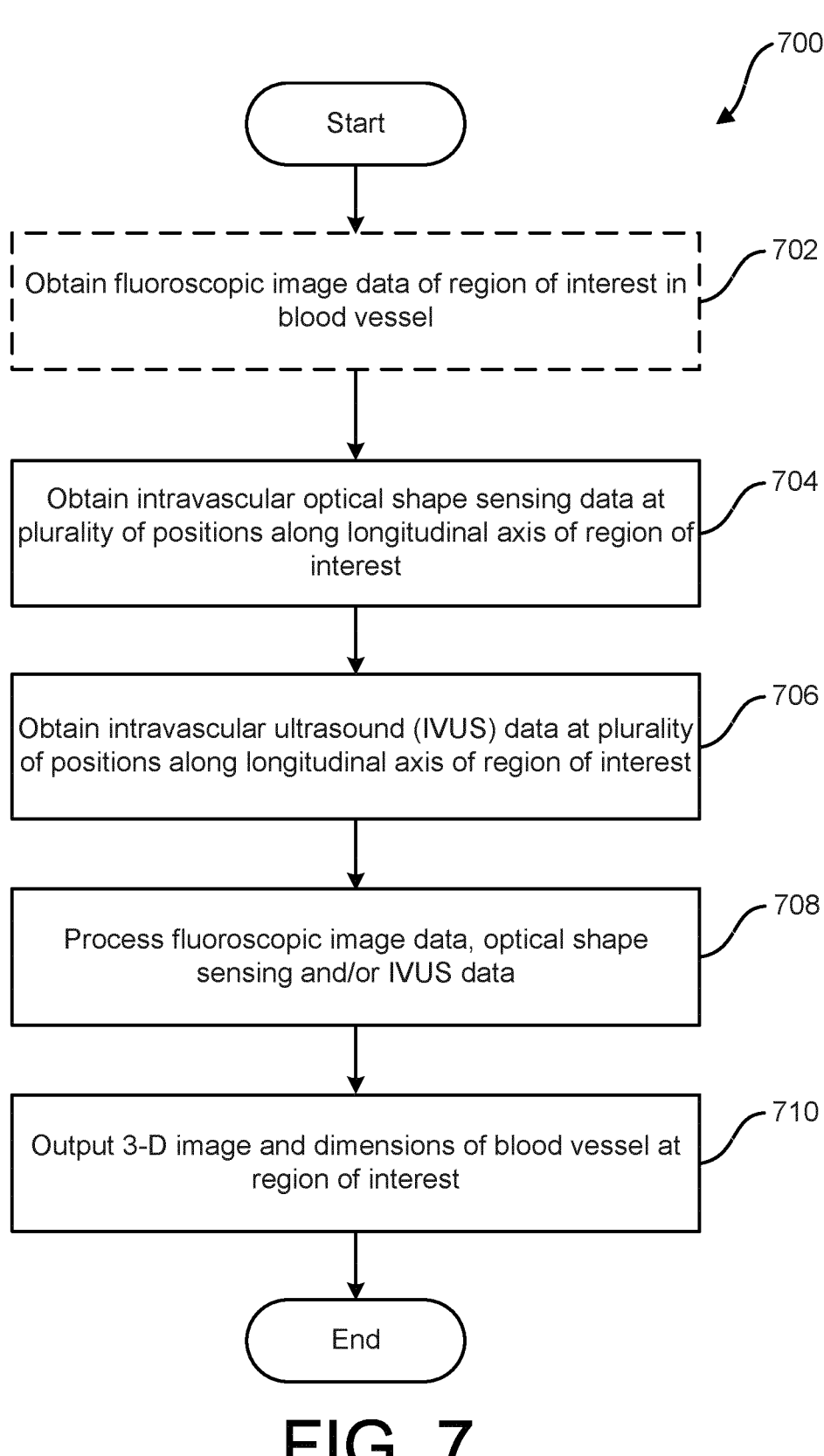
FIG. 7-9 are exemplary flowcharts describing methods of imaging a blood vessel according to aspects of the present disclosure.
Figure 8:
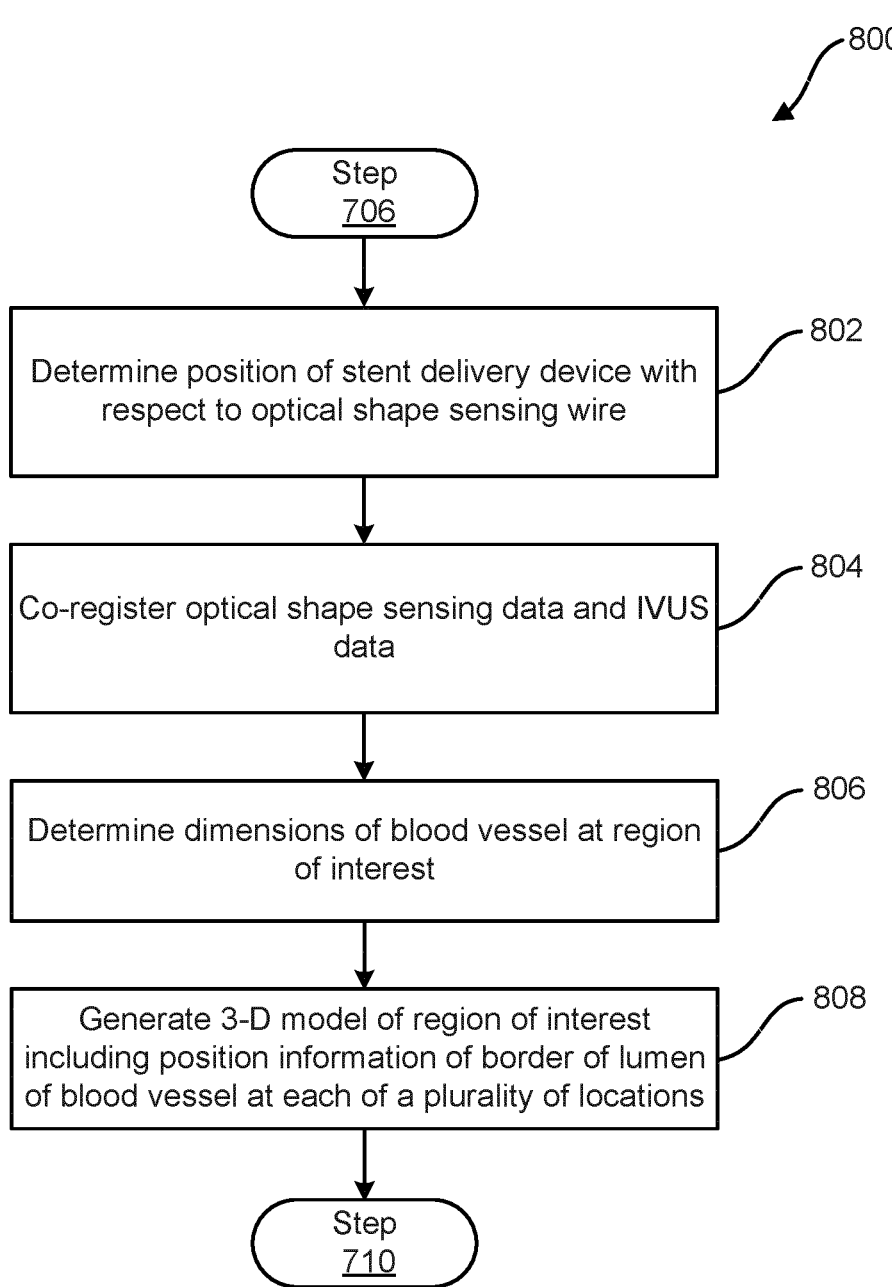
Figure 9:
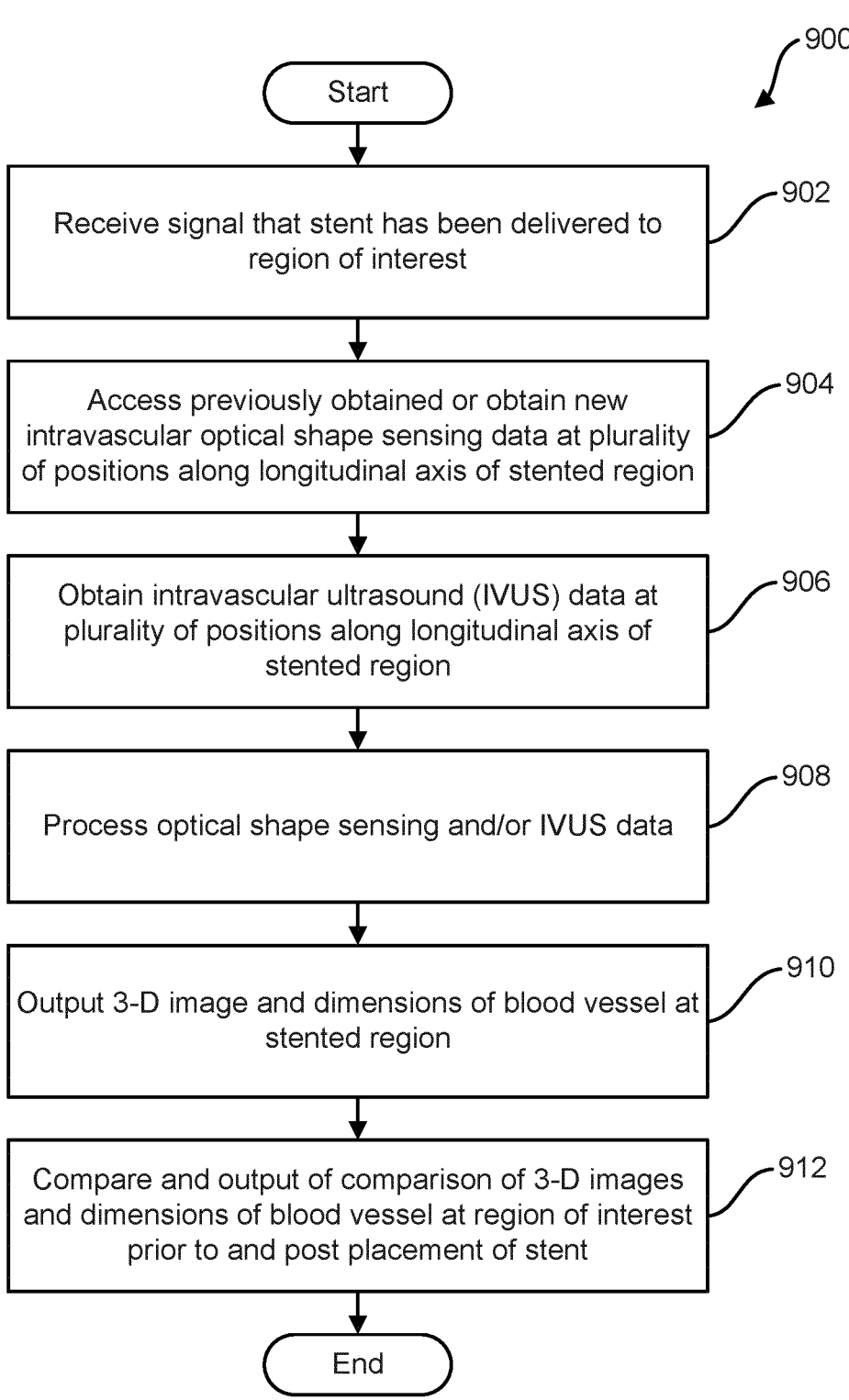

FIGS. 7, 8 and 9 are flow diagrams of a methods 700, 800 and 900, respectively, of imaging a blood vessel according to aspects of the present disclosure. FIG. 7 is a flow diagram of a method 700 for determining the size of an imaged blood vessel and/or a stenosis using geometric measurements (e.g., area, volume, and/or perimeter). The steps of method 700 may be carried out by the OSS wire 300, the IVUS portion of the stent delivery device 200, a separate IVUS device, an angiographic/fluoroscopic imaging system which is indicated as an additional imaging system 160, the computing system of the workstation 405, and/or a combination thereof. In other examples, another invasive intravascular imaging (IVI) system or device, such as an optical coherence tomography (OCT) imaging system and/or a near-infrared spectroscopy (NIRS) system, may perform the steps of method 700, 800, and/or 900. Additionally, and/or alternatively, a non-transitory computer-readable medium (e.g., memory within the computing system of the workstation 105) may include instructions that when executed by one or more processors (e.g., processors within the computing system) may cause the processors to perform the steps of the method 700, 800, and/or 900.

Referring to FIG. 7, in operation, at step 702, the computing system (e.g., one or more processors) obtains fluoroscopic image data of a region of interest in a blood vessel. The fluoroscopic image data may be acquired using an x-ray source. In some examples, the fluoroscopic image data may be acquired before and/or simultaneously with acquiring the intravascular optical shape sensing data and/or IVUS imaging data. For example, a reference fluoroscopic image using a contrast media may be acquired before the OSS data and/or IVUS imaging data is acquired. The reference image may be used, for example, to generally identify the region of interest. The computing system may generate a visual representation of the fluoroscopic image data and output the visual representation to the display 150 separate from the visual representation of a model of the region of interest. The fluoroscopic image data may also be acquired simultaneously as the OSS data and/or IVUS imaging data is acquired. For example, fluoroscopic image data may be acquired while the OSS data and/or IVUS imaging data is acquired during a manual or automated insertion and/or pull back of the OSS wire 300 and/or stent delivery device 200 across the region of interest. As described herein, the fluoroscopic image data and the OSS data and/or IVUS imaging data may be co-registered.

At step 704, the computing system obtains intravascular optical shape sensing data at a plurality of positions across the region of interest. The intravascular optical shape sensing data may be acquired by the OSS wire 300. The region of interest may include an obstruction, such as the stenosis 415, and/or compression, such as a compression caused by pressure from an external artery, that limits blood flow through the vessel 405. In some examples, the OSS sensing module 120 and/or the OSS processing module 125 of the computing system may generate, based on the intravascular optical shape sensing data, an OSS image at each of the plurality of positions across the region of interest and outputting the OSS images to the monitor (e.g., a display device and/other another type of user interface device) 150 separate from the visual representation of a model of the region of interest Referring to FIG. 10, there is depicted a composite 3D image 1000 illustrating a 3D image 1010 of the vasculature generated from the OSS wire 300 along with a series of two-dimensional IVUS images 1020 overlaid on the 3D OSS image 1010.

Referring again to FIG. 7, at step 706 the computing system obtains IVUS imaging data at a plurality of positions across the region of interest. The IVUS imaging data may be acquired using an IVUS component, such as the transducer element 225 disposed on the stent delivery device 200 or separate intravascular device (not shown) that is capable of obtaining IVUS imaging data. In some examples, the IVUS sensing module 130 and/or the IVUS processing module 135 of the computing system may generate, based on the IVUS imaging data, a two-dimensional IVUS image at each of the plurality of positions across the region of interest and outputting the IVUS images to the monitor (e.g., a display device and/other another type of user interface device) 150 separate from the visual representation of a model of the region of interest. Referring again to FIG. 10, the series of the two-dimensional IVUS images 1020 is co-registered with the 3D OSS image 1010 using a common and complementary set of coordinates (e.g., an x, y, z coordinate system) such that each IVUS image 1020 is overlaid and stitched to the 3D OSS image 1010, thereby creating a composite 3D image 1000 illustrating both the OSS image data and IVUS image data in a 3D format, thereby increasing the clinicians understanding and perspective of the region of interest in the vasculature and increasing interventional procedure times related to such region of interest.

The IVUS imaging data at each of the plurality of positions may include a plurality of components corresponding to different frequencies of ultrasound emissions. In some examples, the plurality of components may include a first component corresponding to a first frequency of ultrasound emissions, a second component corresponding to a second frequency with a first gain value, and a third component corresponding to the second frequency with a second gain value. While three components are described herein, it is understood that more than three components, corresponding to different frequencies and/or gain values, may be utilized. For example, the first frequency may be a relatively higher frequency, while the second frequency may be a relatively lower frequency. For example, the first gain value may be a relatively higher gain value, while the second gain value may be a relatively lower gain value. The first and second frequencies may be selected such that the ultrasound emissions behave differently in blood and in tissue. For example, the low frequency may be selected such that the wavelength of the ultrasound emission is larger than a blood cell. This may be beneficial in generating an improved accuracy model of vessel anatomy because soft plaque and blood behave similarly when interrogated by ultrasonic energy. By choosing a low frequency emission, only tissue, and not blood, is imaged by the low frequency emission. The high frequency and low frequency emissions may be used to acquire information about the tissue. In a similar manner, the high gain and low gain values may be selected to optimize acquisition of IVUS imaging data. For example, low frequency, low gain emissions may be used to identify stent struts and calcium, both of which appear as saturated portions in the IVUS image. The IVUS imaging data associated with the low frequency, low gain emissions may be used to more easily identify stent location such that, e.g., how well the stent is opposed to the lumen wall 410 may be readily determined.

Successive ultrasound emissions respectively associated with each of the different frequencies may be separated in time. For example, the transducer element(s) 230 of the stent delivery device 200 and/or another intravascular device may be controlled to transmit ultrasonic energy in the following order: an ultrasound emission associated with the first frequency, an ultrasound emission associated with the second frequency with the first gain value, and an ultrasound emission associated with the second frequency with second gain value. While three ultrasound emissions are described herein, it is understood that more than three ultrasound emissions, e.g., associated with different frequencies and/or gain values, may be utilized. This may improve the efficiency of IVUS imaging data collection by interleaving the emissions with different frequencies and/or gain values. For example, successive high frequency firings may be compared to extract blood flow information. The time between high frequency firings may include low frequency firing(s) to extract information about the position of tissue and/or stents. The particular order disclosed herein is a non-limiting example, and other ultrasound emission algorithms may be implemented in different examples.

Figure 10:
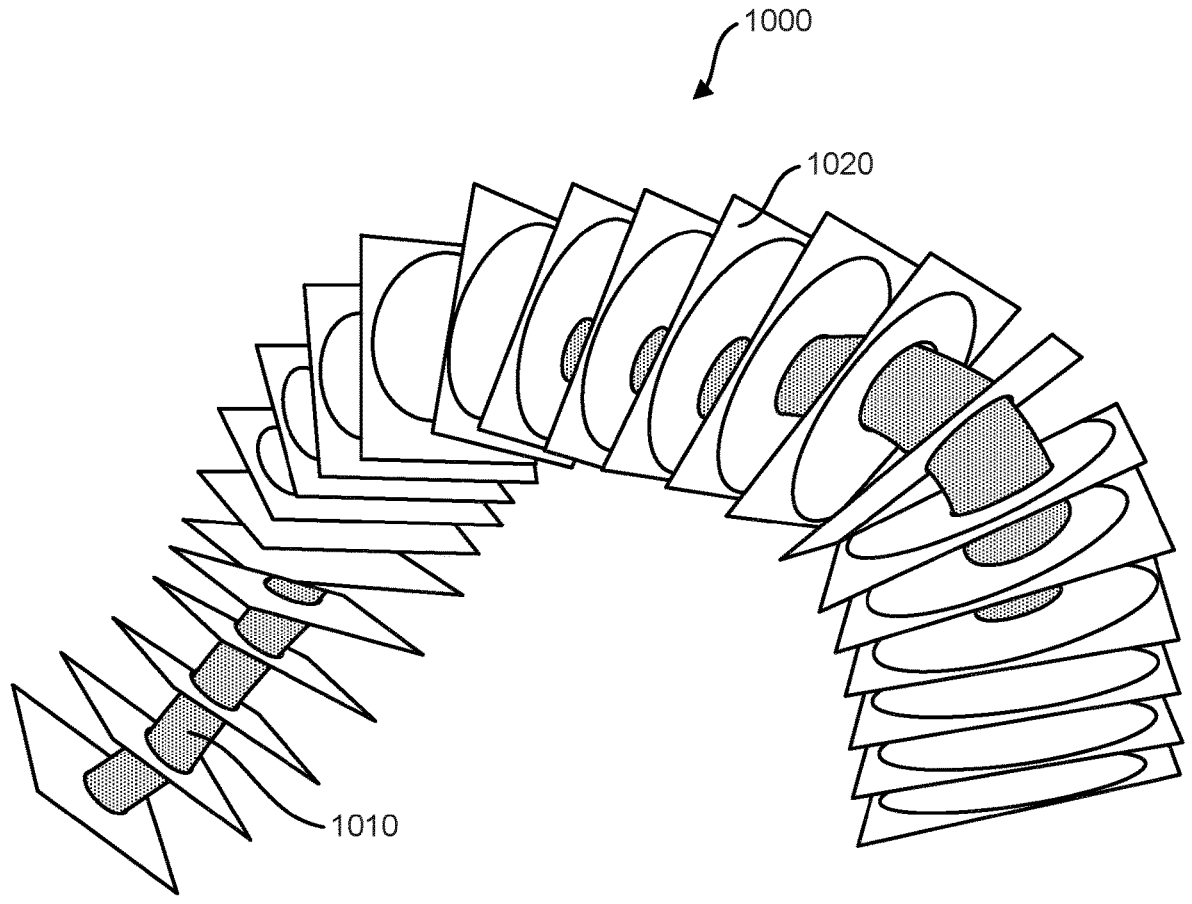
FIG. 10 is an exemplary set of IVUS images stitched to the images obtained from the optical shape sensing wire.

Referring again to FIG. 7, at step 708, the computing system processes the fluoroscopic image data, the OSS data and/or the IVUS imaging data. At step 710, the computing system creates a three-dimensional image and dimensions of the blood vessel, particularly the region of interest, using the fluoroscopic image data, the OSS data and/or the IVUS imaging data as shown in FIG. 10 and discussed hereinabove. One or more sub-steps associated with processing the fluoroscopic image data, the optical shape sensing data and/or the IVUS imaging data is described with reference to the method 800 (FIG. 8). Referring to FIG. 8, at step 802, the stent delivery device 200 is loaded into the subject's vasculature over and onto the OSS wire 300, and the computing system determines, using the fluoroscopic image data, a position of the OSS wire 300 and/or a position of the stent delivery device 200 with respect to the x-ray source at each of the plurality of positions across the region of interest. For example, the orientation marker 230 disposed on the stent delivery device 200 may be identified in the fluoroscopic image data. The computing system may be configured to compute a position of the stent delivery device 200 based on a position of the orientation marker 230 relative to the lumen border 410 in the fluoroscopic image data. The position may be of the stent delivery device 200 along the vessel 405 and/or a rotational position of the stent delivery device 200 within the vessel 405.

Referring to FIG. 5, there is shown another example of determining the position of the stent delivery device 200 (including the stent 215) relative to the OSS wire 300. The stent delivery device 200 may include plural sets 250, 250', etc. of sensors along its longitudinal axis and/or axial length. For example, FIG. 5 depicts one set 250 of sensors in the handle 205 of the stent delivery device 200 and another set 250' of sensors in the distal portion of the shaft 210 of the stent delivery device 200. Although not shown, the stent delivery device 200 may include additional sets of sensors between the handle 205 and the distal portion of the shaft 210. Each set of sensors may include a plurality of sensors 250a, 250b, 250c, etc. The OSS wire may include plural sets 310, 310', etc. of sensors along its longitudinal axis and/or axial length. For example, FIG. 5 depicts one set 310 of sensors at the distal portion of the OSS wire 300 and another set 310' of sensors in a relatively proximal portion of the OSS wire 300. Although not shown, the OSS wire 300 may include additional sets of sensors between the distal and proximal sets of sensors. Each set of sensors may include a plurality of sensors 310a, 310b, 310c, etc.

As the OSS wire 300 enters the lumen of the stent delivery device 200 and one set 310 of sensors in the OSS wire passes a set 250 of sensors in the stent delivery device 200, corresponding signals indicative of the positions of the stent delivery device 200 and the stent 215 relative to the OSS wire 300 will be sent by the stent delivery device 200 and/or the OSS wire 300 to the computing system, including the registration module 140, and the relative positions of the stent delivery device 200 and the stent 215 in relation to the OSS wire 300 will be co-registered. For example, one set 250 of sensors in the stent delivery device 200 may be axial located at the same position axial location that the stent 215 is located. Or the axial position of the stent 215 on the stent delivery device 200 relative to one or more sets of sensors 250 may be stored in memory 115. Additionally, having multiple sensors 250a, 250b, 250c, etc. in each set of sensors in the delivery device 200 and/or multiple sensors 310a, 310b, 310c, etc. in each set of sensors in the OSS wire 300 will allow the computing system to determine the direction (e.g., distally or proximally) that the stent delivery device 200 is traveling. For example, during a stent implantation procedure, the OSS wire 300 will likely be inserted first into the vasculature followed by the stent delivery device 200 being inserted into the vasculature over the OSS wire. When one or more sets 250 of sensors in stent delivery device 200 are at the same axial position of a set of sensors 310 in the OSS wire 300, the relative positions of the stent delivery device 200 and the stent 215 in relation to the OSS wire 300 will be co-registered, and the distal direction or proximal direction of travel of the stent delivery device 200 will be recorded and stored in memory.

Referring again to FIG. 8, at step 804, the computing system, particularly the registration module 140, co-registers the fluoroscopic image data, the OSS data and/or the IVUS imaging data. The simultaneously-acquired fluoroscopic image data, the OSS data and/or the IVUS imaging data may be co-registered such that the location of a particular OSS image and/or IVUS image frame along the vessel 405 may be identified in the fluoroscopic image data. The OSS image and/or IVUS image frame may be appropriately rotated based on the determined position of the stent delivery device 200 such that the position of lumen wall 410 and the diameter of lumen 420, 470 may be determined with improved accuracy. Referring again to FIG. 10, the series of the two-dimensional IVUS images 1020 is co-registered with the 3D OSS image 1010 such that each IVUS image 1020 is overlaid and stitched to the 3D OSS image 1010, thereby creating a composite 3D image 1000 illustrating both the OSS image data and IVUS image data in a 3D format, thereby increasing the clinicians understanding and perspective of the region of interest in the vasculature and increasing interventional procedure times related to such region of interest. As such, the composite 3D image 1000 may be rotated so the clinician can better view the position of the stenosis 415, stenosed region, the lumen wall 410 and the diameter of lumen 420, 470 and other anatomical features of the vasculature 405 or region of interest thereof.

At step 806, the computing system generates and determines dimensions of the blood vessel, particularly at the obstruction or stenosis 415 illustrated in FIG. 6A. The dimensions may be generated using, for example, the determined position of the stent delivery device 200, the co-registered fluoroscopic image data, the OSS image data, the IVUS image data, the composite image 1000 and/or any combination thereof. The dimensions may include position information of the lumen border or wall 410 at each of the plurality of locations across the region of interest. The dimensions may additionally include position information of one or more components of the vessel 405 such as the stenosis 415. For example, the dimensions may include a plurality of points within the vessel 405 and/or around the lumen wall 410. The points may be representative of the position and/or contours of one or more components the vessel 405. The dimensions may additionally include the length of At step 808, the computing system generates a model of the region of interest. The model may be generated using, for example, the determined position of the stent delivery device 200, the co-registered fluoroscopic image data, the OSS image data, the IVUS image data, the composite image 1000 and/or any combination thereof. The model of the region of interest may be a data representation or visual representation of one or more components of the vessel 405. The model may include position information of the lumen border or wall 410 at each of the plurality of locations across the region of interest. The model may additionally include position information of one or more components of the vessel 405 such as blood, plaque, adventitia, calcium, and stent struts. For example, the model may include a plurality of points within the vessel 405 and/or around the lumen wall 410. The points may be representative of the position and/or contours of one or more components the vessel 405. The model may additional include characterization data associated with each of the plurality of points. The characterization data may identify the components of the vessel 405. The data representation of the model may be used by the computing system to automatically make pre-treatment determinations, including the proper length and diameter of a stent, the proper positioning of a stent strut relative to the lumen wall 410.

In some examples, generating the model of the region of interest may include determining the boundary between blood and tissue within the blood vessel. The blood-tissue boundary may be determined using IVUS image data representative of blood changing randomly from frame-to-frame and/or acquired using ultrasound emissions having different frequencies and/or gain values that cause blood to be less visible. The boundary determination may additionally consider measurements from the co-registered fluoroscopic image data. Thus, the computing system may compute measurements, such as the diameter, length, area, perimeter, and/or volume of the vessel lumen. The boundary determination may additionally consider a calculated rotational position of the intravascular device relative to the x-ray source as indicated by the catheter-orienting markers visible in the fluoroscopic image data. The computing system 306 may output an indication of the determined position of the blood-tissue boundary.

In some examples, generating the model of the region may include determining the boundary between vessel media and surrounding adventitia. The media-adventitia boundary may be determined based on the determined position of the boundary of blood and tissue of the blood vessel. The boundary determination may additionally consider IVUS image data. In particular, the IVUS image data associated with ultrasound emissions having a frequency that penetrates the vessel lumen (e.g., such that the media and adventitia are interrogated) may be used to determine the boundary. The boundary determination may also consider a determined position of a stent strut relative to the border of a lumen. The computing system may output an indication of the determined position of the media-adventitia boundary.

The visual representation of the model may include optical shape sensing images, IVUS images, fluoroscopic images, and/or a combination thereof, that are output to the display 150. The visual representation may be two-dimensional but preferably three-dimensional when viewed on the display 150. The visual representation may include the improved accuracy position and borders of one or more components of the vessel 405 as described herein. The one or more components of the vessel 405 may be variously colored to improve clarity (e.g., the blood may be colored differently from the tissue, the plaque may be colored differently than the tissue, etc.). The visual representation may present the co-registered fluoroscopic image data, optical shape sensing data and the IVUS imaging data in an interactive manner. For example, selecting a position along the region of interest of the vessel 405 in the fluoroscopic image or the optical shape sensing image may bring up the corresponding IVUS image frame. The OSS image and IVUS image frames of the model may be rotated based on the position of the stent delivery device 200.

In some examples, the visualization may include generating a composite OSS and IVUS images using the optical shape sensing data and the IVUS image data associated with different frequencies and/or different gain values. The composite OSS and IVUS images may be relatively clearer with respect to the position of blood, plaque, adventitia, calcium, stent struts, etc. than the OSS and IVUS images generated using a single frequency and/or gain value. The composite OSS and IVUS image may be generated by computing the features of each pixel in an IVUS image frame, on a pixel-by-pixel basis. The features and/or content of each pixel may be based on the IVUS image data associated with different frequencies and/or different gain values. The features of each pixel may include numerical value(s) associated with echoes from the reflected ultrasound waves, whether the pixel corresponds to blood and/or tissue, what particular type of tissue the pixel corresponds to, etc. A composite pixel value may be produced by combining the information from the IVUS image data associated with different frequencies and different gain values. Combining the information in this manner may advantageously provide an optimal pixel value to filter out noise, emphasize anatomical structure, and thereby aid physicians in image interpretation. In some examples, the composite OSS and IVUS images may include an overlay having color indications of determined positions of a blood-tissue boundary, a media-adventitia boundary, and/or stent strut locations. The computing system may output the composite OSS and IVUS images.

In some examples, the visualization may include generating a longitudinal representation of the region of interest. The longitudinal representation may be a longitudinal cross section of the blood vessel at any angle, similar to the image longitudinal display (ILD) described in U.S. patent application Ser. No. 14/038,106, filed Sep. 26, 2013, the entirety of which is herein incorporated by reference. The longitudinal representation may be generated using the IVUS image data associated with different frequencies and different gain values, and/or the composite IVUS images. The computing system may output the longitudinal representation. In some examples, the longitudinal representation may include an overlay having color indications of determined positions of a blood-tissue boundary, a media-adventitia boundary, and/or stent strut locations.

In some examples, the computing system may determine a position of a minimal lumen area in the blood vessel. The minimal lumen area may occur where a stenosis 415 causes the most narrowing of the blood vessel. The position of the minimal lumen area may be calculated based on the blood-tissue boundary. The longitudinal representation may include an indication of the position of minimal lumen area. In some examples, the computing system may provide an indication, on the longitudinal representation, of a region of stenosis proximate to the minimal lumen area. In some examples, the method 700 may include determining a position of the blood vessel that is un-stenosed and closest to the region of stenosis. The computing system may calculate an area, diameter, and/or perimeter of the determined position using the generated model. Additionally, or alternatively, the computing system may calculate a volume between two determined positions using the generated model. The computing system may calculate a stent length/diameter based on the calculated area, diameter, volume, and/or perimeter as described below. The suggested stent diameter and length may expand the region of stenosis to have a diameter similar to the diameter of the blood vessel proximal and distal of the region of stenosis. The computing system may output the suggested stent diameter and length.

As described herein, the OSS image(s), IVUS images and/or fluoroscopic image data may be displayed separately from the model or composite image of the region of interest. In some examples, the composite image, OSS image(s), IVUS images and/or fluoroscopic image data may be displayed at a different time than the model of the region of interest (e.g., before and/or after stent deployment). In some examples, the OSS image(s), IVUS images and/or fluoroscopic image data output to a different portion of the display 150 as the composite image or model of the region of interest. For example, the OSS image(s), IVUS images and/or fluoroscopic image data may be positioned proximate to the composite image or model of the region of interest.

Figure 6B:
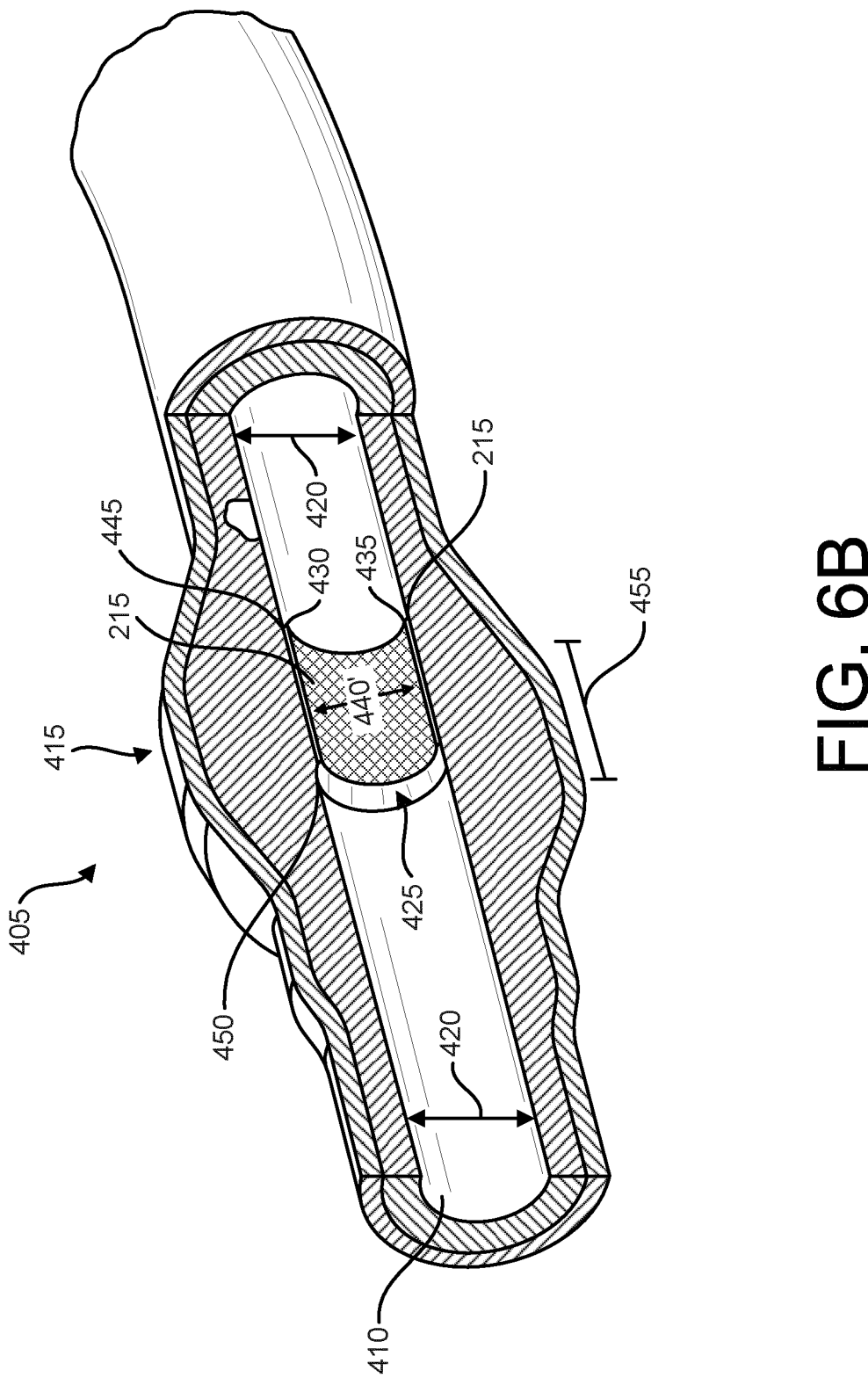
FIG. 6B is an exemplary, partial cross-sectional perspective view of a blood vessel having a stent placed adjacent to and restraining the stenosis according to an example of the present disclosure.

Referring again to FIGS. 7 and 8, the methods 700 and 800 are performed by the computing system prior to deployment of the stent 215. Referring to FIG. 3, the stent 215 is coupled to and disposed on the shaft 210 at the distal portion the stent delivery device 200 as it is inserted into vessel 405 (FIG. 6A) over the OSS wire 300 and the stent 215 is axially aligned and placed adjacent the stenosis 415. In FIG. 4, the stent 215 is detached from the shaft 210 of the stent delivery device 200 and expanded adjacent the stenosis 415 as shown in FIG. 6B. The outer sheath 240 includes a sensor 270 at its distal end, and the shaft 210 of the stent delivery device 200 includes a sensor 275. Upon the outer sheath 240 being retracted proximally relative to the self-deploying stent 215 and the shaft 210 (or the shaft 210 and the self-deploying stent 215) being extended distally of the outer sheath 240, the sensor 270, 275 overlap, and one or both sensors send a signal to the workstation 105, wherein the sensor signal(s) are indicative that the stent 215 has been deployed within the vasculature of the subject 400 as shown in FIG. 6B. Hence, this signal may be referred to as a stent-deployment signal.

Referring to FIG. 9, there is depicted a method 900 of analyzing the region of interest in the vasculature after the stent 215 has been deployed and comparing the post-implantation data to the pre-implantation data. For example, step 902 includes receiving a signal indicative that the stent 215 has been deployed within the region of interest in the vasculature of the subject 400. As mentioned above, to deploy the stent the outer sheath 240 is retracted proximally relative to the self-deploying stent 215 while the shaft 210 and OSS wire remain substantially stationary or fixed. So, immediately prior to deployment of the stent 215, the system 100 has recorded the relative positions of the OSS wire 300 and stent deployment device 200, as well as calculated the dimensions of the region of interest of the vasculature and created a three-dimensional model or composite image thereof. Assuming the OSS wire 300 remains substantially stationary during retraction of the outer sheath 240 and expansion of the stent 215, step 904 includes accessing the stored intravascular optical shape sensing data at a plurality of position along the longitudinal axis of the region of interest, particularly the stenosed region where the stent 215 has been implanted. If the OSS wire 300 translates or rotates during retraction of the outer sheath 240 and expansion of the stent 215, step 904 includes obtaining new intravascular optical shape sensing data at a plurality of position along the longitudinal axis of the region of interest, particularly the stenosed region where the stent 215 has been implanted.

Step 906 of the method 900 in FIG. 9 includes obtaining IVUS imaging data at a plurality of position along the longitudinal axis of the region of interest, particularly the stenosed region where the stent 215 has been implanted. Step 908 includes processing the OSS data and the IVUS imaging data, including co-registering the data. Step 910 includes determining dimensions of the region of the vasculature where the stent 215 has been implanted and generating a three-dimensional model or composite image of the region of the stented vasculature. Step 912 includes comparing the dimensions and model of the region of interest immediately prior to and immediately subsequent to stent deployment. The precise comparisons of the dimensions and the three-dimensional models and composite images is made possible by the use of the OSS wire 300 and the stent delivery device 200 which remain in the vasculature (and without being removed). That is, the OSS wire 300 creates the three dimensional image of the vasculature, and because the OSS wire 300 remains in the vasculature during stent deployment, the system can accurately determine the relative positions of the OSS wire 300 and stent delivery device 200, thereby ensuring that same region of interest is analyzed and compared. For example, a determined length, diameter, perimeter and 2D or 3D shape of the stenosis 415 or stenosed region of the vasculature just prior to and after stenting may be output in response to a user input received at the computing system, without human interpretation of the IVUS imaging data and/or the fluoroscopic image data.

For instance, a variety of measurements, size characteristics and/or equations related to the stenosed region can be compared using the 3D composite images and models obtained prior to and after stent deployment. For example, a distance between the proximal shoulder 450 and the distal shoulder 445 may be computed using the composite 3D image or model. The length of the stent 215 may be determined to be substantially similar to the distance between the proximal shoulder 450 and the distal shoulder 445 or slightly larger or slightly smaller. In various examples, different computational methods may be carried out using the generated model of the region of interest to determine the length of the stenosed region and stent. In another example, the computing system may determine a diameter or height 440 of the lumen 410 at the stenosed region 415 within the blood vessel 405. The computing system may also determine one or more equations to use to calculate a derived diameter (e.g., intrinsic or true diameter) associated with the stenosed region or stented region within the blood vessel. For example, geometrically derived diameter measurements (e.g., true diameter measurements) provide a method to determine diameter measurements for a vascular contour, area, or volume regardless of the contour shape (e.g., convex/concave) and without having to check the contour point combinations to identify minimum/maximum diameters. This is especially relevant to concave contour scenarios which make direct diameter measurements from the vascular contours harder to obtain.

In other words, based on at least one 2D or 3D cross-section image of the blood vessel 405 (e.g., from the generated model or composite image), the computing system determines an area, volume, and/or perimeter of a portion (e.g., a cross-sectional area) of the blood vessel. For example, as mentioned previously, the computing system may use a border algorithm to determine (e.g., locate) the lumen border. After determining the location lumen border, the computing system may calculate the area (e.g., the number of pixels within the lumen border) and/or the perimeter (e.g., the number of pixels of the lumen border). Additionally, and/or alternatively, the computing system may use the generated model and/or multiple different cross-sectional images across the region of interest to determine the volume. For example, the computing system may calculate area at multiple different regions (e.g., regions with stenosis and regions without stenosis). Then, the computing system may determine the length of the region of interest, including the length of the regions with and/or without stenosis. Using the length and/or area(s), the computing system may calculate the volume of the vessel 405.

In some examples, the portion of the blood vessel may be a cross-sectional area of the position of the blood vessel with the minimal lumen area (e.g., where the stenosis causes the most narrowing of the blood vessel and/or the minimum cross-sectional area of the blood vessel). The portion with the minimal lumen area may be denoted by the position within the blood vessel associated with height 440 in FIG. 6A. In other examples, the computing system determines the area, volume, and/or perimeter of another portion of the blood vessel, such as the portion denoted by the position within the blood vessel associated with diameters 420 and/or 470.

After determining the area, volume, and/or perimeter, the computing system determines one or more equations (e.g., a perimeter equation, an area equation, and/or a volume equation) to use to determine (e.g., calculate) a derived diameter of the blood vessel. The derived diameters are obtained prior to and after stent deployment, and the computing system suggests or recommend one ore more diameters for comparison. In some examples, the computing system and/or the display 150 may include a user input device (e.g., keyboard, mouse, touchscreen). The computing system may receive a user input (e.g., from a doctor) indicating a position within the blood vessel via the interface 155. The computing system may determine the area and/or perimeter of the portion (e.g., cross-section) of the blood vessel associated with the position indicated by the user input. In other words, the doctor may want an area/perimeter measurement of a cross-sectional area within the blood vessel that may or might not be at the minimal lumen area position. After, the computing system may determine the area and/or perimeter at the indicated position. Then, the computing system may determine to use the area and/or perimeter equation to calculate the derived diameter of the blood vessel.

In other examples, the computing system might not receive a user input and may automatically determine the derived diameter of the blood vessel. For example, the computing system may calculate a volume of the blood vessel, including portions of the blood vessel with stenosis and portions without. In some instances, the computing system may only calculate the volume of the blood vessel with the stenosis.

In some examples, the computing system may determine the one or more equations (e.g., a volume equation of a circle and/or ellipse) based on being able to determine and/or determining a location (e.g., part) within a patient where the OSS and/or IVUS image was taken. For example, the computing system determines the derived diameter of the vessel (e.g., associated with the stent) based on the OSS data and the IVUS imaging data (e.g., the generated model or composite image) and/or the one or more equations. For example, the computing system 306 may use the one or more equations determined at step 602 above to determine the derived diameter. The one or more equations may include:

$$P = 2\pi R \tag{1}$$

$$A \text{ (circle)} = \pi R^2 \tag{2}$$

$$V \text{ (circle)} = HA = H\pi R^2 \tag{3}$$

$$A \text{ (ellipse)} = \pi R_1 R_2 \tag{4}$$

$$V \text{ (ellipse)} = \pi H R_1 R_2 \tag{5}$$

In the above equations (1)-(5), P represents perimeter, R represents radius of a circle, $R_1$ and $R_2$ represent the minor and major axes of an ellipse, V represents volume of a circle or an ellipse, A represents area of a circle or an ellipse, and H represents height. Then, in some examples, given the length of a vascular contour (i.e. the perimeter P) and assuming a circular geometry for the vessel and/or stent, the derived diameter $D_p$ may be derived from equation (1):

$$D_p = 2R = P/\pi \tag{6}$$

In other words, the computing system 306 may use equation (6) above to determine the derived diameter of the blood vessel based on the perimeter measurement from the generated model of the blood vessel.

In other examples, given the area (e.g., A) enclosed by a vascular contour (e.g. the lumen or vessel boundaries of the blood vessel) and assuming a circular geometry for the vessel and/or stent, the derived diameter $D_a$ may be derived from equation (2) and/or equation (4):

$$D_a = 2R = 2\sqrt{\left(\frac{A}{\pi}\right)} \qquad (7)$$

In other words, the computing system 306 may use equation (7) above to determine the derived diameter of the blood vessel based on the area measurement from the generated model of the blood vessel.

In yet other examples, given the volume (e.g., V) enclosed by a stack vascular contour (e.g., the lumen or vessel boundaries of the blood vessel) and assuming a circular geometry for the vessel and/or stent, the derived diameter be derived from equation (3) and/or equation (5):

$$D_v = 2R = 2\sqrt{\left(\frac{V}{H\pi}\right)} \qquad (8)$$

In other words, the computing system 306 may use equation (8) above to determine the derived diameter of the blood vessel based on the volume measurement from the generated model of the blood vessel. In some instances, the volume of a stack of vascular contours (e.g., V) may be calculated using Simpson's rule. In such instances, H is the length of vessel represented by the stack of contours (e.g., the length of vessel covered by the imaging frames from which the vessel contours are obtained).

In some examples, the computing system 306 may use additional and/or alternative equations to determine the derived diameter of the blood vessel. For example, the computing system 306 may determine the derived diameter based on adding a correction term (e.g., an error estimation value) to one or more of the equations above (e.g., equations (1)-(8)).

In some variations, due to imaging conditions and the difficulty in imaging at an orthogonal cross section, an intrinsic diameter based on volume built from successive imaging cross sections can be more representative of the derived diameter measurement that can be related to stent sizing. For example, the OSS data and/or IVUS imaging data may include multiple different OSS data and/or IVUS images (e.g., successive slices) of the vessel. The computing system may use the one or more equations (e.g., area/perimeter equations) to determine diameters for each of these images. Then, the computing system may average them to determine the derived diameter. For example, the computing system may use a perimeter equation and/or area equation to determine multiple different diameters. The computing system may then average the multiple different diameters to determine a derived diameter. In some instances, the computing system may determine the derived diameter of the stent using the average diameter (e.g., from the multiple different composite images) and a length of the vessel.

In some examples, the computing system may determine two or more equations to use to calculate the derived diameter. For example, the computing system may initially determine the derived diameter from the volume of the blood vessel (e.g., using equation (6) above). Additionally, and/or alternatively, the computing system may determine the derived diameter from the area and/or perimeter of the blood vessel (e.g., using equations (5) and/or (6) above). For instance, after determining the derived diameter from the volume, the computing system 306 may receive user input indicating a portion of the blood vessel and/or indicating an equation to use for the derived diameter. Based on the user input, the computing system may determine the derived diameter using the perimeter and/or area. In other examples, the computing system may initially determine the derived diameter from the area. After, the computing system may determine the derived diameter from the volume and/or perimeter based on the user input. In yet other examples, the computing system may initially determine the derived diameter from the perimeter. After, the computing system may determine the derived diameter from the volume and/or area based on the user input.

In some variations, the calculated derived diameters for the area, perimeter, and/or volume may be different. In such variations, the computing system may determine a confidence interval or value for each of the derived diameters. The confidence interval may indicate the likelihood that the calculated derived diameter relates to the actual diameter of the blood vessel. In some instances, the computing system may determine the derived diameters using more than one method and then determine whether the different derived diameters are within an acceptable tolerance (e.g., pre-determined/pre-defined threshold). If so, the computing system may use the derived diameters from one of the methods. If not, the computing system may repeat the steps above to determine new derived diameters. For example, the computing system may calculate the derived diameters using geometric measurements (e.g., area, volume, and/or perimeter equation) from two different angles (e.g., one from a clockwise geometry and another from a counterclockwise geometry). Additionally, and/or alternatively, the computing system may determine the derived diameters using one or more geometric measurements, pixel counting, and/or user-input (e.g., user defined input regarding areas within the composite image).

In some instances, the computing system may use the derived diameters from at least one of the area, perimeter, and/or volume equations to determine accuracy of the derived diameters (e.g., whether the derived diameter is an accurate representation of the diameter of the vessel). For example, if the derived diameters between the area, perimeter, and/or volume equations are different, the computing system may determine whether the derived diameters are within a pre-determined range of each other. If not, the computing system may determine new derived diameters from the equations. In other words, the equations may be used as a check to determine whether they accurately show the actual diameter of the blood vessel. If the differences between them exceed the pre-determined range, then the computing system may determine new derived diameters (e.g., from another cross-sectional area of the vessel) to use for the stent.

The natural tendency of vessels may be to assume a circular shape, and thus the computing system may be able to apply the equations (6), (7), and/or (8) to calculate the derived diameter (e.g., diameter of the vessel). The circular shape assumption also applies to stents which are circular and sized based on their diameter and length. The above methods and systems are especially beneficial when the vessel is deformed, and/or its contours are not circular. In such scenarios, the contour perimeter, the area enclosed by a contour, and the volume enclosed by a stack of contours may still be generated. Using any of those measurements, the derived diameter of the vessel may be derived based on the equations (6), (7), and/or (8).

The foregoing discussion has been presented for purposes of illustration and description. The foregoing is not intended to limit the disclosure to the form or forms disclosed herein. For example, referring again to FIGS. 7, 8 and 9, the methods 700, 800 and 900, the present disclosure generally describe methods 700 and 800 being performed by the computing system prior to deployment of the stent 215 and method 900 being performed during and after stent deploy-ment. However, the present disclosure contemplates that methods 700 and 800 being performed by the same stent delivery device 200, the OSS wire 300 and the computing system both prior to and after deployment of the stent, wherein a 3-D image and dimensions of the blood vessel are determined for the same region of interest (same location for the same region of interest), wherein the region of interest does not include the stent prior to treatment, and the region of interest includes the stent after treatment because deploy-ment the stent is the treatment. In this scenario, method 900 would include step 902, step 904 would include accessing the so-called previously obtained 3-D images and dimen-sions of the blood vessel for the pre-treatment and post-treatment region of interest (with and without the stent), and step 912 would include comparing and outputting a com-parison of the 3-D images and dimensions of the blood vessel at region of interest both prior to and post stent deployment (pre-treatment and post-treatment).

In the foregoing Summary for example, various features of the disclosure are grouped together in one or more aspects, examples, and/or configurations for the purpose of streamlining the disclosure. The features of the aspects, examples, and/or configurations of the disclosure may be combined in alternate aspects, examples, and/or configura-tions other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configura-tion. Thus, the following claims are hereby incorporated into this Detailed Description, with each claim standing on its own as a separate preferred embodiment of the disclosure.

Moreover, though the description has included descrip-tion of one or more aspects, examples, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, examples, and/or configurations to the extent permitted, including alternate, interchangeable and/or equivalent structures, functions, ranges or steps to those claimed, whether or not such alternate, interchange-able and/or equivalent structures, functions, ranges or steps are disclosed herein, and without intending to publicly dedicate any patentable subject matter.

What is claimed is:

1. A stent delivery system comprising:
    a shape sensing wire configured to produce shape sensing data representative of a region of interest in a vessel in a subject;
    a stent delivery device disposed over the shape sensing wire, wherein the stent delivery device comprises a stent and an imaging element disposed distally of the stent, wherein the imaging element is configured to produce intravascular ultrasound imaging data representative of the region of interest for deploying the stent in the region of interest;
    a fluoroscopy imaging device configured to produce fluo-roscopic image data corresponding to the region of interest; and
    a computing system comprising:
        one or more processors; and
        non-transitory memory storing instructions that, when executed by the one or more processors, cause the one or more processors to:
            receive a plurality of first signals corresponding to the shape sensing data;
            receive a plurality of second signals corresponding to the intravascular ultrasound imaging data;
            co-register the first signals, the second signals, and the fluoroscopic image data with one another;
            process the co-registered first signals, second signals and fluoroscopic image data to generate a pre-deployment three-dimensional model of the region of interest;
            perform at least one geometric measurement of the region of interest using the pre-deployment three-dimensional model before deployment of the stent in the region of interest;
            based on the at least one geometric measurement, determine a pre-deployment size characteristic of the region of interest;
            receiving a stent-deployment signal indicative of the stent being deployed;
            receive a plurality of third signals corresponding to the shape sensing data after receiving the stent-deployment signal;
            receive a plurality of fourth signals corresponding to the intravascular ultrasound imaging data after receiving the stent-deployment signal;
            co-register the third signals and the fourth signals;
            process the co-registered third and fourth signals to generate a post-deployment three-dimensional model of the region of interest;
            perform at least one geometric measurement of the region of interest using the post-deployment three-dimensional model after the deployment of the stent in the region of interest;
            based on the at least one geometric measurement, determine a post-deployment size characteristic of the region of interest;
            calculate a comparison of the pre-deployment size characteristic and the post-deployment size char-acteristic; and
            provide, to a monitor, the comparison.

2. The stent delivery system of claim 1, wherein the stent delivery device comprises a sensor, wherein the sensor produces a stent deployment signal upon retraction of a sheath over the stent delivery device.

3. The stent delivery system of claim 1, wherein each of the pre-deployment size characteristic and the post-deploy-ment size characteristic is a derived diameter of the region of interest.

4. The stent delivery system of claim 3, wherein the at least one geometric measurement of the region of interest comprises at least one of an area, a volume, or a perimeter of the region of interest.

5. The stent delivery system of claim 4, wherein the derived diameter is determined based on the area of the region of interest.

6. The stent delivery system of claim 4, wherein the derived diameter is determined based on the volume of the region of interest.

7. The stent delivery system of claim 4, wherein the derived diameter is determined based on the perimeter of the region of interest.

8. The stent delivery system of claim 3, wherein the derived diameter is determined based on at least two of an area, a volume, and a perimeter of the region of interest.

9. The stent delivery system of claim 1, wherein the stent delivery device comprises:

an outer sheath configured to cover the stent during introduction of the stent into the vessel; and a shaft configured to slidably move within the outer sheath while carrying the stent, enabling deployment of the stent when the stent extends past a distal end of the outer sheath.

10. The stent delivery system of claim 9, wherein the stent delivery device further comprises:

a first sensor positioned on the outer sheath at a distal end of the outer sheath; and a second sensor positioned on the shaft proximal to the stent, wherein at least one of the first sensor or the second sensor produces a stent deployment signal when the first sensor and the second sensor overlap in response to relative movement between the outer sheath and the shaft to enable the deployment of the stent.

11. The stent delivery system of claim 1, wherein the region of interest includes an obstruction in the vessel that results in a restriction to blood flow through the vessel.

12. The stent delivery system of claim 11, wherein the obstruction comprises a stenosis.

13. The stent delivery system of claim 11, wherein the obstruction comprises a compression caused by pressure from an external artery that limits the blood flow through the vessel.

14. A system comprising:

one or more processors; and non-transitory memory storing instructions that, when executed by the one or more processors, cause the one or more processors to:

obtain a plurality of first signals corresponding to shape sensing data for a region of interest in a vessel of a subject;

obtain a plurality of second signals corresponding to intravascular ultrasound imaging data for the region of interest;

obtain fluoroscopic image data corresponding to fluoroscopic images of the region of interest acquired simultaneously with acquisition of the shape sensing data and/or the intravascular ultrasound imaging data;

co-register the first signals, the second signals, and the fluoroscopic image data with one another;

process the co-registered first and second signals to generate a pre-deployment three-dimensional composite image of the region of interest;

perform at least one geometric measurement of the region of interest using the pre-deployment three-dimensional composite image before deployment of the stent in the region of interest;

based on the at least one geometric measurement, determine an initial volume of blood capable of passing through the region of interest;

receiving a stent-deployment signal indicative of a stent being deployed in the region of interest;

receive a plurality of third signals corresponding to the shape sensing data after receiving the stent-deployment signal;

receive a plurality of fourth signals corresponding to the intravascular ultrasound imaging data after receiving the stent-deployment signal;

co-register the third signals and the fourth signals;

process the co-registered third and fourth signals to generate a post-deployment three-dimensional composite image of the region of interest;

perform at least one geometric measurement of the region of interest using the post-deployment three-dimensional composite image after the deployment of the stent in the region of interest;

based on the at least one geometric measurement, determine an updated volume of blood capable of passing through the region of interest;

calculate a comparison of the initial volume of blood and the updated volume of blood; and provide a comparison signal indicative of the comparison.

15. The system of claim 14, wherein execution of the instructions by the one or more processors further cause the one or more processors to receive a stent deployment signal from a sensor upon retraction of a sheath over the stent for deployment of the stent.

16. The system of claim 14, wherein execution of the instructions by the one or more processors further cause the one or more processors to co-register fluoroscopic image data with the first signals and the second signals, and process the co-registered fluoroscopic image data, first signals and second signals to generate the pre-deployment three-dimensional composite image of the region of interest.

17. A non-transitory computer readable medium storing instructions for execution by one or more processors incorporated into a system, wherein execution of the instructions by the one or more processors cause the one or more processors to:

obtain initial optical shape sensing data for a blood vessel;

obtain initial intravascular imaging data for the blood vessel;

obtain fluoroscopic image data corresponding to fluoroscopic images of the blood vessel acquired simultaneously with the initial optical shape sensing data and/or the initial intravascular imaging data;

co-register the initial optical shape sensing data, the initial intravascular imaging data, and the fluoroscopic image data with one another;

generate an initial three-dimensional model of the blood vessel from the co-registered initial optical shape sensing data, initial intravascular imaging data, and fluoroscopic image data;

perform at least one geometric measurement of the blood vessel using the initial three-dimensional model after deployment of the stent in the region of interest;

determine an initial derived diameter associated with a portion of the initial three-dimensional model based on the at least one geometric measurement;

obtain subsequent intravascular imaging data for the blood vessel;

co-registering the initial optical shape sensing data and the subsequent intravascular imaging data;

generate a subsequent three-dimensional model of the blood vessel from the co-registered initial optical shape sensing data and subsequent intravascular imaging data;

perform at least one geometric measurement of the blood vessel using the subsequent three-dimensional model after the deployment of the stent in the region of interest;

determine a subsequent derived diameter associated with a portion of the subsequent three-dimensional model based on the at least one geometric measurement; and provide, to a monitor, a signal representative of a comparison of the initial derived diameter and the subsequent derived diameter.

* * * * *